(12) United States Patent
Nimer et al.

(10) Patent No.: US 8,010,208 B2
(45) Date of Patent: Aug. 30, 2011

(54) MICROELECTRODE, APPLICATIONS THEREOF AND METHOD OF MANUFACTURING

(75) Inventors: Emad Nimer, Nazareth (IL); Nabil Jadaon, Nazareth Ilit (IL); Fauzi Silbaq, Shfaram (IL)

(73) Assignee: Nano Biosensors Ltd., Nazareth (IL)

( * ) Notice: Subject to any disclaimer, the term of this patent is extended or adjusted under 35 U.S.C. 154(b) by 505 days.

(21) Appl. No.: 11/922,969

(22) PCT Filed: Jun. 6, 2006

(86) PCT No.: PCT/IL2006/000653
§ 371 (c)(1),
(2), (4) Date: Dec. 27, 2007

(87) PCT Pub. No.: WO2006/131912
PCT Pub. Date: Dec. 14, 2006

(65) Prior Publication Data
US 2009/0248113 A1 Oct. 1, 2009

Related U.S. Application Data

(60) Provisional application No. 60/687,344, filed on Jun. 6, 2005.

(51) Int. Cl.
*A61N 1/05* (2006.01)
(52) U.S. Cl. .................................. 607/118; 607/115
(58) Field of Classification Search .................. 607/116, 607/115, 118; 600/372, 378; 977/931
See application file for complete search history.

(56) References Cited

U.S. PATENT DOCUMENTS

| | | | |
|---|---|---|---|
| 4,762,135 A | 8/1988 | Van der Puije et al. | |
| 4,842,703 A | 6/1989 | Class et al. | |
| 5,515,848 A * | 5/1996 | Corbett et al. | 600/377 |
| 6,980,865 B1 * | 12/2005 | Wang et al. | 607/121 |
| 7,006,859 B1 * | 2/2006 | Osorio et al. | 600/378 |
| 7,162,308 B2 | 1/2007 | O'Brien et al. | |
| 2003/0083724 A1 | 5/2003 | Jog et al. | |
| 2004/0098074 A1 | 5/2004 | Erickson et al. | |
| 2004/0111141 A1 | 6/2004 | Brabec et al. | |
| 2007/0060815 A1 | 3/2007 | Martin et al. | |

OTHER PUBLICATIONS

Wise et al. "Wireless Implantable Microsystems: High-Density Electronic Interfaces to the Nervous System" Proceedings of the IEEE, vol. 92 No. 1, Jan. 2004.*
Communication Pursuant to Article 94(3) EPC Dated Jul. 13, 2009 From the European Patent Office Re.: Application No. 06745131.0.
International Preliminary Report on Patentability Dated Dec. 21, 2007 From the International Bureau of WIPO Re.: Application No. PCT/IL2006/000653.

(Continued)

*Primary Examiner* — Carl H Layno
*Assistant Examiner* — Natasha N Patel

(57) ABSTRACT

An electrode device is disclosed. The electrode device comprises an electrically conductive core of micrometric size coated by at least one electrically isolating layer. The electrically conductive core comprises a substrate coated by at least one metallic layer having a nanometric pattern thereon and being at least partially exposed at a tip of the electrically conductive core.

21 Claims, 11 Drawing Sheets
(5 of 11 Drawing Sheet(s) Filed in Color)

OTHER PUBLICATIONS

International Search Report Dated Mar. 26, 2007 From the International Searching Authority Re.: Application No. PCT/IL06/00653.
Supplementary European Search Report and the European Search Opinion Dated Mar. 27, 2009 From the European Patent Office Re.: Application No. 06745131.0.
Written Opinion Dated Mar. 26, 2007 From the International Searching Authority Re.: Application No. PCT/IL06/00653.
Communication Pursuant to Article 94(3) EPC Dated Jul. 13, 2009 From the European Patent Office Re.: Application No. 06745131.0.
Official Action Dated Jan. 6, 2010 From the US Patent and Trademark Office Re.: U.S. Appl. No. 11/922,969.
Official Action Dated Dec. 30, 2009 From the US Patent and Trademark Office Re.: U.S. Appl. No. 11/922,969.

* cited by examiner

MICROELECTRODE, APPLICATIONS THEREOF AND METHOD OF MANUFACTURING

RELATED APPLICATIONS

This Application is a National Phase of PCT Patent Application No. PCT/IL2006/000653 having International Filing Date of Jun. 6, 2006, which claims the benefit of U.S. Provisional Patent Application No. 60/687,344 filed on Jun. 6, 2005. The contents of the above Applications are all incorporated herein by reference.

FIELD AND BACKGROUND OF THE INVENTION

The present invention relates to microelectrodes and, more particularly, but not exclusively, to microelectrodes useful for medical purposes, such as, but not limited to, monitoring of electrical activity and stimulation of neurons, e.g., in the central nervous system.

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex as well as the basal ganglia, the thalamus and the motor cortex cooperatively interact to facilitate motor function control.

A movement disorder is a neurological disturbance that involves one or more muscles or muscle groups. Movement disorders include Parkinson's disease, Huntington's Chorea, progressive supranuclear palsy, Wilson's disease, Tourette's syndrome, epilepsy, and various chronic tremors, tics and dystonias. Different clinically observed movement disorders can be traced to the same or similar areas of the brain. Abnormalities of basal ganglia, for example, are postulated as a causative factor in diverse movement disorders. More specifically, deficiency of the neurotransmitter dopamine as the consequence of degenerative, vascular or inflammatory changes in the basal ganglia is postulated as the reason for development of Parkinson's disease. Clinical symptoms of the Parkinson's disease, such as rhythmical muscular tremors, rigidity of movement, Destination, droopy posture and masklike facies, are known to appear after 50-60% neuronal loss has occurred in the substantia nigra.

Tremors are characterized by abnormal, involuntary movements. An essential tremor is maximal when the body part afflicted (often an arm or hand) is being used, for example when attempts at writing or fine coordinated hand movements are made. A resting tremor is common in Parkinson's disease and in syndromes with Parkinsonian features. A resting tremor is maximal when the extremities are at rest. Often, when a patient attempts fine movement, such as reaching for a cup, the tremor subsides. Dystonias are involuntary movement disorders characterized by continued muscular contractions which can result in twisted contorted postures involving the body or limbs. Causes of dystonia include biochemical abnormalities, degenerative disorders, psychiatric dysfunction, toxins, drugs and central trauma.

There are a wide variety of treatment modalities for neurological disease in general and movement disorders in particular. These include the use of medicaments (e.g., dopaminergic agonists or anticholinergic agents), tissue ablation (e.g., pallidotomy, thalamotomy, subthalamotomy and other radiofrequency lesioning procedures) and tissue transplantation (e.g., animal or human mesencephalic cells).

Another traditional approach for controlling neurological disease is by electrical stimulation of a predetermined neurological region. The use of electrical stimulation for treating neurological disease, including movement disorders, has been widely discussed in the literature. It has been recognized that electrical stimulation holds significant advantages over radiofrequency lesioning, inasmuch as radiofrequency lesioning can only destroy nervous system tissue. In many instances, the preferred effect is to stimulate to increase, decrease or block neuronal activity. Electrical stimulation permits such modulation of the target neural structures and, equally importantly, does not require the destruction of nervous tissue.

A variety of brain-controlled disorders, including movement disorders, have been found treatable via electrical treatment with deep brain stimulation (DBS). Many disabling symptoms of the Parkinson's disease, including tremor, muscular rigidity, dyskinesia, bradykinesia, and loss of postural stability are known to be effectively treated with a DBS electrode, when traditional medical treatment fails. The neurostimulation blocks the symptoms of the disease resulting in increased quality of life for the patient.

Generally DBS involves placement of a permanent DBS electrode through a burr hole drilled in the patient's skull, and then applying appropriate stimulation through the electrode to the physiological target. To date, DBS has been successfully used in the Vin nucleus, the globus pallidus internal segment (GPi), and the subthalamic nucleus (STN). DBS is particularly effective for relieving of tremors, rigidity, bradykinesia, and dyskinesia. The step of electrode placement during the DBS procedure is very critical, and has been the subject of much attention and research. It is recognized that finding the deep brain target and then placing the permanent electrode such that it efficiently stimulates the target is of utmost importance.

A typical DBS system comprises a pulse generator operatively connected to the brain by one or more permanent electrodes implanted within the patient's brain at a precise location, such that the electrode or electrodes are optimally and safely positioned for the desired stimulation. The electrode is placed in the nervous tissue by a stereotaxic operation whereby the electrode tip is placed in the desired target with an accuracy of a few millimeters. To determine the stereotaxic coordinates of the desired target, a stereotaxic frame is fixed onto the patient's head. The frame functions as an external Cartesian coordinate system with X, Y and Z axes. Once the stereotaxic frame is fixed onto the head, an imaging procedure, such as a computerized tomography (CT) scan or a magnetic resonance imaging (MRI) is performed. The resulting CT or MR images display the brain anatomy and the external stereotaxic frame, and the appropriate coordinate set of any brain region is determined.

It is recognized that if the electrode is located as little as 2 mm away from the desired target, ineffective stimulation results due to several reasons: (i) failure to capture control of the group of neurons, (ii) stimulation of non-desirable areas resulting in unpleasant stimulation, or (iii) necessity for higher stimulus intensities to produce the desired effect resulting in reduced battery life of the implantation, or an any combination of these or other reasons. At least for these reasons, targeting the specific neurons of interest requires high precision and allowance for variability among patients.

Typically, the process of implantation of a DBS electrode follows a step-wise progression of (i) initial estimation of target localization based on imaged anatomical landmarks; (ii) intra-operative microanatomical mapping of key features associated with the intended target of interest; (iii) adjustment of the final target of implantation by appropriate shifts in three dimensional space; and (iv) implantation of the DBS electrode with contacts located at the final desired target.

Thus, for each electrode to be implanted, a burr hole is made in the patient's skull under local anesthesia, and a burr-hole ring is affixed to each opening. Subsequently, a microelectrode is introduced through the burr-hole ring. Test stimulation is performed and a neurologist is simultaneously assessing the stimulation effect on the parkinsonian symptoms of the awake patient. Extracellular recordings are performed, and neuronal activity is displayed. This technique is based on the premise that neurons in one nucleus maybe differentiated from neurons in neighboring nuclei by their electro physiological signatures. If no effect is determined, the microelectrode is advanced stepwise towards the target area along a different trajectory. Test stimulation and neurological assessment are performed at each step. Once the level of maximal stimulation effect is determined, the microelectrode is replaced with a permanent macroelectrode which is affixed to the burr-hole rings. The macroelectrode is connected to a pulse generator which is typically implanted subcutaneously in the pectoral region.

Several DBS systems have been developed over the years. To this end see, e.g., U.S. Pat. Nos. 5,515,848, 5,843,093, 6,560,472, 6,799,074, 6,011,996, 6,094,598, 6,760,626, 6,950,709 and 7,010,356; U.S. Patent Applications No. 20020022872, 20020198446, 20050015130, 20050165465, 20050246004, 2005055064, 20060069415, 20060041284, 20060089697; and International Patent Applications, Publication Nos. WO 1999/036122, WO 2002/011703 and WO 2006/034305.

The above systems, however, suffer from many limitations. Traditionally, the microelectrode used during the stepwise targeting is durable for at most a few stimulations. Since for each trajectory several micro-stimulations are needed, the microelectrode has to be replaced several times during the targeting step. It is recognized that the replacement of the micro-electrode results in severe complication of the procedure because the replaced electrode never return to its original coordinate.

Due to the complex structure of the different nuclei, the size of the macroelectrode, and the inability to place the macroelectrode in the exact center of the nuclei, a large volume of the brain is stimulated, leading to the deactivation of large regions outside the target nucleus and only a partial coverage of the target nucleus. It is appreciated that this limitation results in only partial alleviation of the Parkinson symptoms. Moreover, stimulation of neighboring brain areas results in various complications, such as undesired side effects, include tingling sensation (paresthesia), worsening of symptoms, speech problems (dysarthria, dysphasia), dizziness or lightheadedness (disequilibrium), facial and limb muscle weakness or partial paralysis (paresis), involuntary muscle contractions (dystonia, dyskinesia), movement problems or reduced coordination, jolting or shocking sensation and numbness (hypoesthesia).

It was shown that macro-stimulation during DBS results in contradictory responses in different zones of the STN. While the stimulated nucleus shows inhibition and/or decreased activity [Benazzouz et al., 1995, Neurosci Let 189: 77-80; Benazzouz et al., 2000, Neuroscience 99:289-295; Boraud et al., 1996, Neurosci Let 215:17-20; and Dotrovsky et al., 2000, J. Neurophysiol 84: 570-574.], the efferent nuclei of the stimulated nucleus indicate increase in the activity [Anderson et al., (2003, J. Neurophysiol 89:1150-1160; Hashimoto et al., 2003, J Neurosci 23:1916-1923; Maurice et al., 2003, J Neurosci 23: 9929-9936; Windels et al., 2000, Eur J Neurosci 12:4141-4146; and Windels et al., 2003, J Neurosci Res 72: 259-267].

Although numerous attempts have been made to improve the procedure, e.g., by providing a macroelectrode with several leads, the improvement is still far from being satisfactory. This is primarily due to the size of the macroelectrode which it too large for performing accurate specific stimulation.

The main reason for the lack of suitable electrode for accurate specific stimulation is the difficulty in the manufacturing process. The mechanical and electrical properties of a microelectrode depend on the materials of the microelectrode. Unfortunately, the mechanical and electrical properties of the microelectrode are conflicting features because materials which posses good mechanical properties have less than optimal electrical properties and vice versa. For example, tungsten can be used to manufacture a stiff microelectrode, but such microelectrode is known to undergo corrosion. Platinum-iridium, on the other hand, is a noble metal-alloy which tolerates much against corrosion but is not stiff as tungsten. Moreover, the price of noble metals is expensive, especially iridium.

Numerous attempts have been made to manufacture microelectrodes having improved mechanical and electrical properties. To this end see, e.g., U.S. Pat. Nos. 4,927,515, 4,959, 130, 5,178,743, 5,256,205, 5,685,961, 6,301,492, 6,186,090, 6,217,716, 6,343,226 and 6,799,074, and U.S. Patent Application Nos. 20050255242 and 20020041158.

The use of rough metals-alloy films with high dielectric constant such as titanium nitride (TiN) coating on different metal substrate has found increasing interest because of its metal-like conductivity and excellent mechanical and chemical properties. In addition, such metals-alloy films can be coated by the use of physical vapor deposition (PVD), chemical vapor deposition (CVD) processes and atomic layer deposition (ALD). However, heretofore these metals-alloys were only used to manufacture thick substrates, because only thick substances posses sufficient mass and heat capacitance to tolerate the high temperature of the PVD process.

There is thus a widely recognized need for, and it would be highly advantageous to have a microelectrode devoid of the above limitations.

SUMMARY OF THE INVENTION

According to one aspect of the present invention there is provided an electrode device, comprising an electrically conductive core of micrometric size coated by at least one electrically isolating layer. The electrically conductive core comprises a substrate coated by at least one metallic layer having a nanometric pattern thereon and being at least partially exposed at a tip of the electrically conductive core.

According to another aspect of the present invention there is provided an electrode assembly, comprising at least one bundle of the electrode devices described herein.

According to yet another aspect of the present invention there is provided an implantable stimulation device for delivery of electrical stimuli to a neurological location The implantable stimulation device comprises: at least one bundle of flexible electrode devices disposed in a guiding encapsulation; and a plurality of microwires, connected to the bundle(s) of flexible electrode devices such that electrical communication is established in an addressable manner between each microwire and at least one electrode device.

According to still another aspect of the present invention there is provided an implantable device for communicating with an implantable stimulation device The implantable device comprises an implantable device body having therein a multi-channel system capable of providing stimulation signals and receiving sensing signals via a plurality of microwires, and a memory medium communicating with the multi-channel system and configured to store, at least temporarily, a stimulation protocol and/or the sensing signals. The multi-channel system is designed and configured to provide the stimulation signals based on the sensing signals and using the stimulation protocol.

According to an additional aspect of the present invention there is provided a system for delivery of electrical stimuli to a neurological location. The system comprises: (a) a first implantable device, which comprises at least one bundle of flexible electrode devices disposed in a guiding encapsulation, and a plurality of microwires connected to the bundle(s) of flexible electrode devices such that electrical communication is established in an addressable manner between each microwire and at least one electrode device; and (b) a second implantable device, which comprises an implantable device body having therein a multi-channel system as described herein, and a memory medium communicating with the multi-channel system as described herein.

According to further features in preferred embodiments of the invention described below, the system further comprises a wireless communication system for establishing communication between the memory medium and an external data processor.

According to still further features in the described preferred embodiments the data processor is supplemented by an algorithm capable of calculating the stimulation protocol based on the sensing signals, the stimulation protocol being transmitted by the data processor via the wireless communication system to be stored in the memory medium.

According to still further features in the described preferred embodiments the system further comprises a mechanism for controlling pressure applied on the plurality of microwires to extrude at least a portion of the flexible electrode devices outward from the guiding encapsulation.

According to still further features in the described preferred embodiments the second implantable device comprises a rechargeable power source.

According to still further features in the described preferred embodiments the system further comprises a recharging device designed and configured to remotely recharge the rechargeable power source via the wireless communication system.

According to yet an additional aspect of the present invention there is provided a method of implanting an implantable stimulation device for delivery of electrical stimuli to a neurological location, the method comprises: providing the implantable stimulation device; implanting the implantable stimulation device at the neurological location; applying pressure on the plurality of microwires to extrude at least a portion of the flexible electrode devices outward from the guiding encapsulation; and removing the guiding encapsulation.

According to still an additional aspect of the present invention there is provided a method of calculating a stimulation protocol, comprises providing sensing signals representing neurological activity at a neurological location, mapping the sensing signals to provide a neurological activity map, and using the neurological activity map for calculating the stimulation protocol.

According to a further aspect of the present invention there is provided a method of manufacturing an electrode device, the method comprises: at least partially coating a substrate of micrometric size by a at least one metal alloy so as to provide at least one metallic layer having a nanometric pattern thereon, thereby providing an electrically conductive core; and coating the metallic layer(s) by at least one electrically isolating layer in a manner such that the metallic layer(s) is at least partially exposed at a tip thereof; thereby forming the electrode device.

According to further features in preferred embodiments of the invention described below, one or more metallic layers are applied on the substrate by physical vapor deposition.

According to still further features in the described preferred embodiments one or more metallic layers are applied on the substrate by electrochemical plating.

According to still further features in the described preferred embodiments on or more electrically isolating layers are applied on the metallic layer(s) by physical vapor deposition.

According to still further features in the described preferred embodiments one or more electrically isolating layers are applied on the metallic layer(s) by pulling technique.

According to still further features in the described preferred embodiments the coating of the metallic layer(s) comprises masking the tip so as to ensure the exposure of the tip.

According to still further features in the described preferred embodiments the method further comprises exposing the tip subsequently to the coating the metallic layer(s).

According to still further features in the described preferred embodiments the method further comprises applying an electrochemical etching procedure to the metallic layer(s) so as to increase the porosity thereof.

According to still further features in the described preferred embodiments the method further comprises activating the metallic layer(s) so as to ensure that a surface of the metallic layer(s) is electrochemically active.

According to still further features in the described preferred embodiments the method further comprises aging the metallic layer(s) to remove unstable residues therefrom.

According to still further features in the described preferred embodiments the method further comprises tapering the tip prior to the step of at least partially coating the substrate.

According to still further features in the described preferred embodiments the method further comprises forming at least one intermediate layer on the substrate and/or on the metallic layer(s).

According to yet a further aspect of the present invention there is provided a method of manufacturing an electrode assembly, the method comprises: providing a plurality of substrates and repeating the steps of the method of manufacturing the electrode device claim for each substrate to provide a plurality of electrode devices; and assembling the plurality of electrode devices thereby forming the electrode assembly.

According to further features in preferred embodiments of the invention described below, the implantable device further comprises a multi-channel connector, mountable on an external organ near the neurological location and configured to establish multi-channel communication with the bundle of electrode devices via the plurality of microwires.

According to still further features in the described preferred embodiments the method further comprises mounting the multi-channel connector on the external organ.

According to still further features in the described preferred embodiments the bundle(s) of flexible electrode devices are disposed in the guiding encapsulation in a manner such that when a pressure is applied on the plurality of microwires, the flexible electrode devices fan outward from the guiding encapsulation to define a target region which is substantially larger than a cross-sectional area of the guiding encapsulation.

According to still further features in the described preferred embodiments the guiding encapsulation is removable.

According to still further features in the described preferred embodiments the guiding encapsulation comprises a plurality of disconnectable parts.

According to still further features in the described preferred embodiments the plurality of microwires comprises stiff microwires.

According to still further features in the described preferred embodiments the bundle(s) of electrode devices comprises electrode devices of different diameters.

According to still further features in the described preferred embodiments the electrically conductive core is tapered.

According to still further features in the described preferred embodiments the electrically conductive core further comprises at least one intermediate layer.

According to still further features in the described preferred embodiments the intermediate layer(s) is interposed between the substrate and the metallic layer(s).

According to still further features in the described preferred embodiments the metallic layer(s) comprises a plurality of metallic layers and the intermediate layer(s) is interposed between two adjacent metallic layers of the plurality of metallic layers.

According to still further features in the described preferred embodiments the intermediate layer(s) is interposed between the metallic layer(s) and the at least one electrically isolating layer.

According to still further features in the described preferred embodiments the substrate comprises a conductive polymer.

According to still further features in the described preferred embodiments the substrate comprises a conductive metal.

According to still further features in the described preferred embodiments the nanometric pattern is selected so as to ensure that the surface area of the electrically conductive core is larger than the geometric surface area of the electrically conductive core by at least one order of magnitude.

According to still further features in the described preferred embodiments the nanometric pattern is selected so as to ensure that the surface area of the electrically conductive core is larger than the surface area of the substrate by at least one order of magnitude.

According to still further features in the described preferred embodiments the electrode device is capable of sensing electrical signals at a signal-to-noise ratio of at least 300.

According to still further features in the described preferred embodiments the electrically isolating layer comprises a biocompatible polymer.

According to still further features in the described preferred embodiments the metallic layer(s) is capable of preventing penetration of macromolecules therethrough.

According to still further features in the described preferred embodiments the metallic layer(s) has a porous structure.

According to still further features in the described preferred embodiments the metallic layer(s) comprises a metal alloy nitride compound.

According to still further features in the described preferred embodiments the metal alloy comprises at least two metals selected from the group consisting of a transition metal, a rare earth metal and an alkali metal.

According to still further features in the described preferred embodiments the metals alloy comprises a noble metal.

According to still further features in the described preferred embodiments the metals alloy comprises a metal capable of produce a stable oxide element.

According to still further features in the described preferred embodiments the metals alloy comprises a reactive metal.

According to still further features in the described preferred embodiments the metallic layer(s) comprises at least one intermediate metallic layer and at least one superficial metallic layer.

According to still further features in the described preferred embodiments the at least one intermediate metallic layer comprises a gold layer.

According to still further features in the described preferred embodiments the at least one intermediate metallic layer comprises a platinum layer.

According to still a further aspect of the present invention there is provided a magnetron coating system for coating a substrate with at least one sputter material. The system comprises: a magnet for generating a magnetic flux within a deposition chamber; a gas delivery unit, for providing a flow of sputter gas into the deposition chamber; and a plurality of local magnet assemblies positioned outside the chamber and respectively defining a plurality of treating zones within the chamber. Each treating zone comprises a sputter target material and at least one anode in proximity to the sputter target material. The system further comprises a movable plate configured to hold the substrate and operable to move within the chamber from one treating zone to the other, thereby to effect a non-continues sputtering deposition process for coating the substrate by contacting the substrate with sputter material plasma generated in the plurality of treating zones.

According to further features in preferred embodiments of the invention described below, the plurality of treating zones are spaced apart to form a plurality of cooling zones therebetween, each of the cooling zones being characterized by a sufficiently low temperature, sputter material plasma concentration and electromagnetic draft force.

According to still further features in the described preferred embodiments at least two of the plurality of treating zones comprises different sputter target materials.

According to still further features in the described preferred embodiments the system further comprises a cooling mechanism for maintaining a sufficiently low temperature within each of the plurality of treating zones.

The present invention successfully addresses the shortcomings of the presently known configurations by providing an electrode device, applications thereof and method and system for manufacturing the electrode device.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
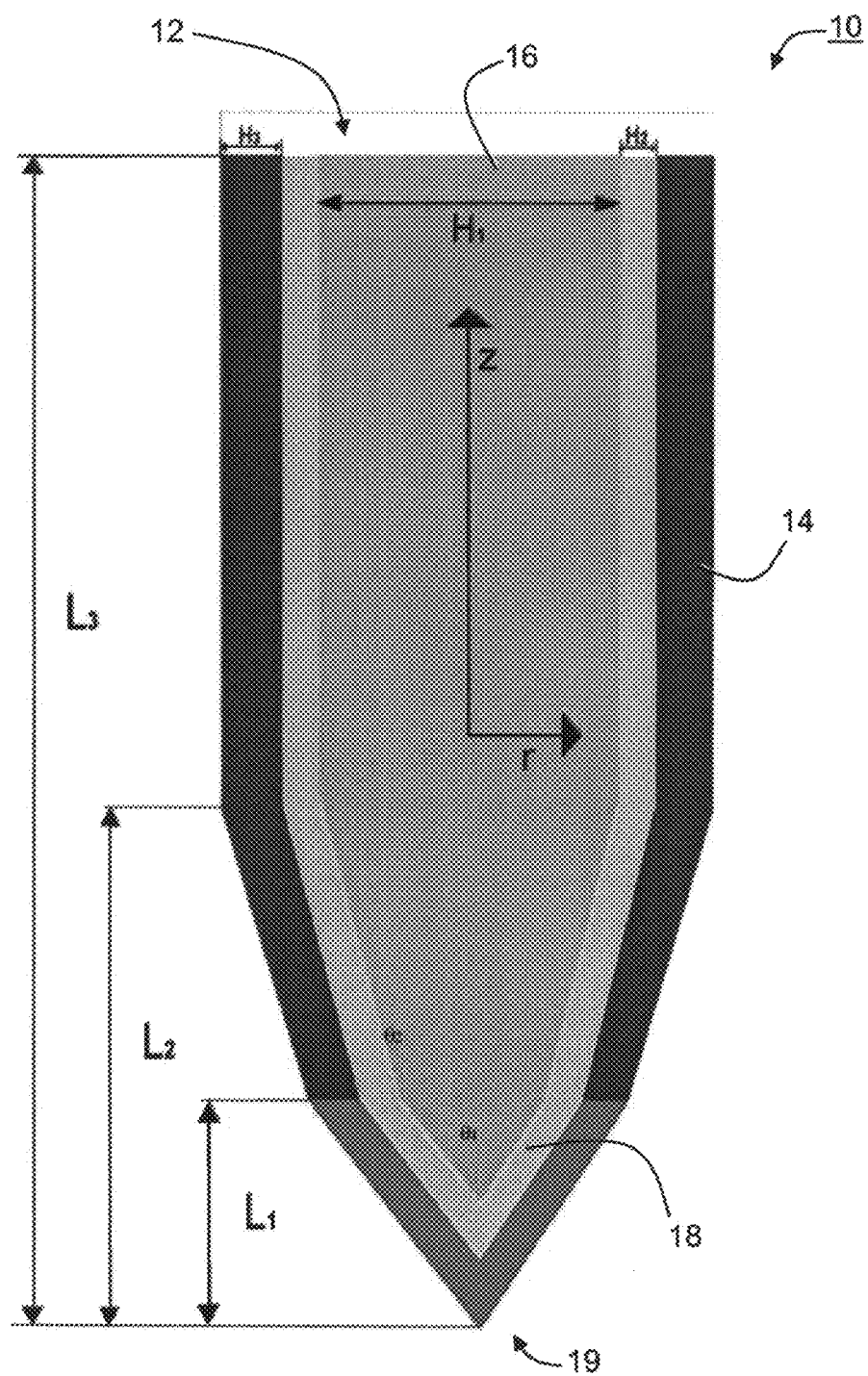
Figure 1B:
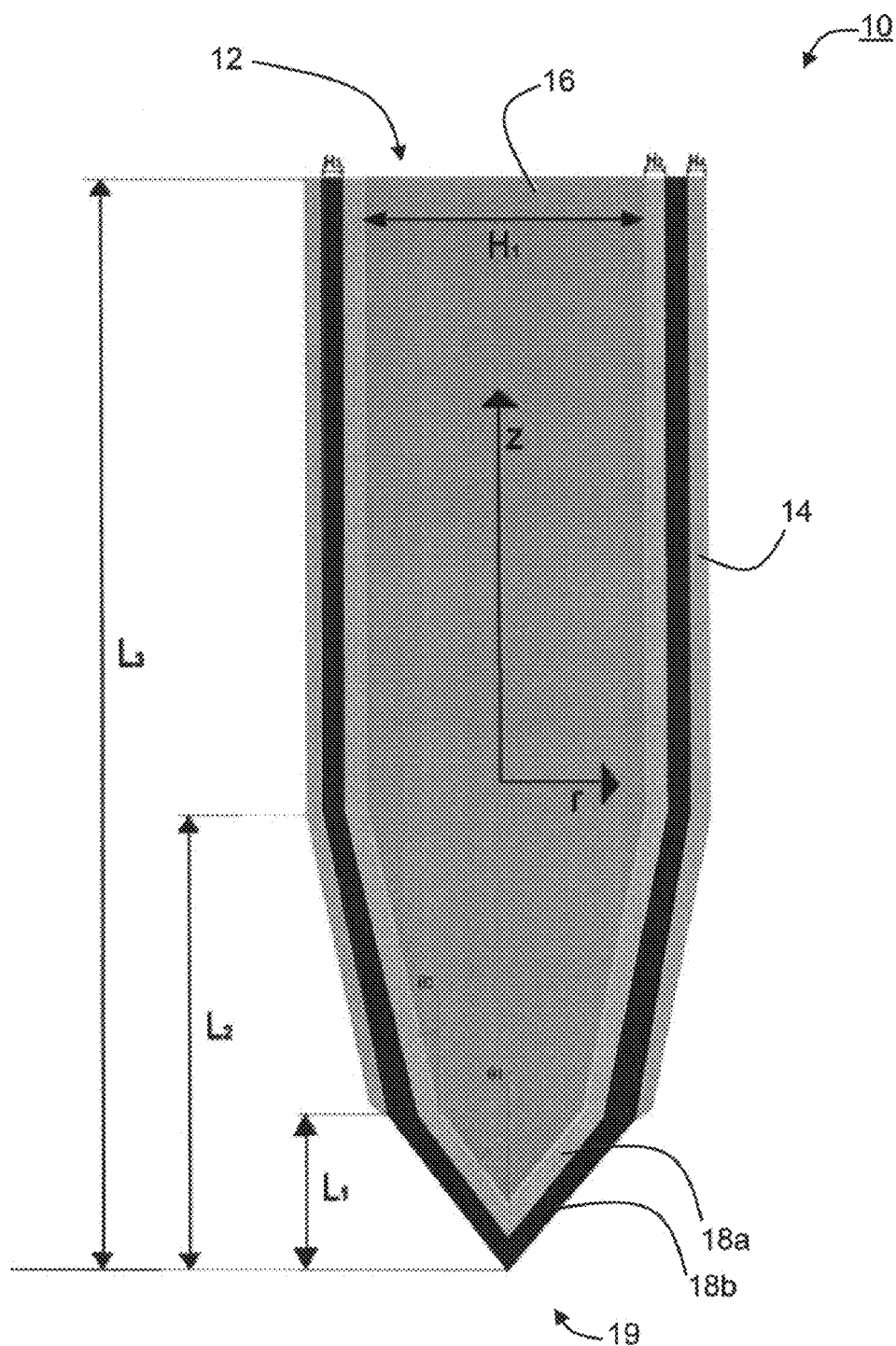
Figures 1C, 1D:
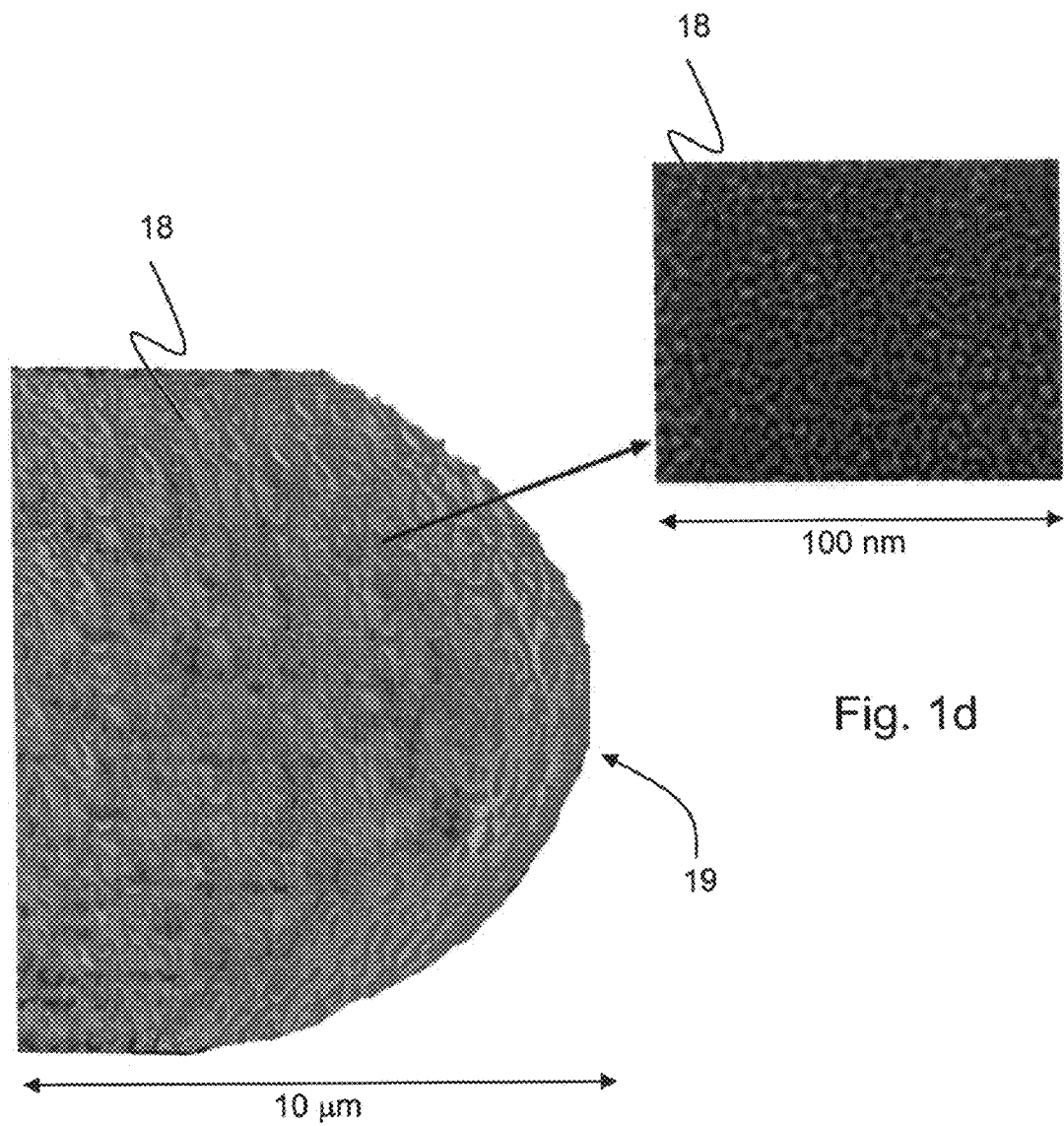
Figure 1E:
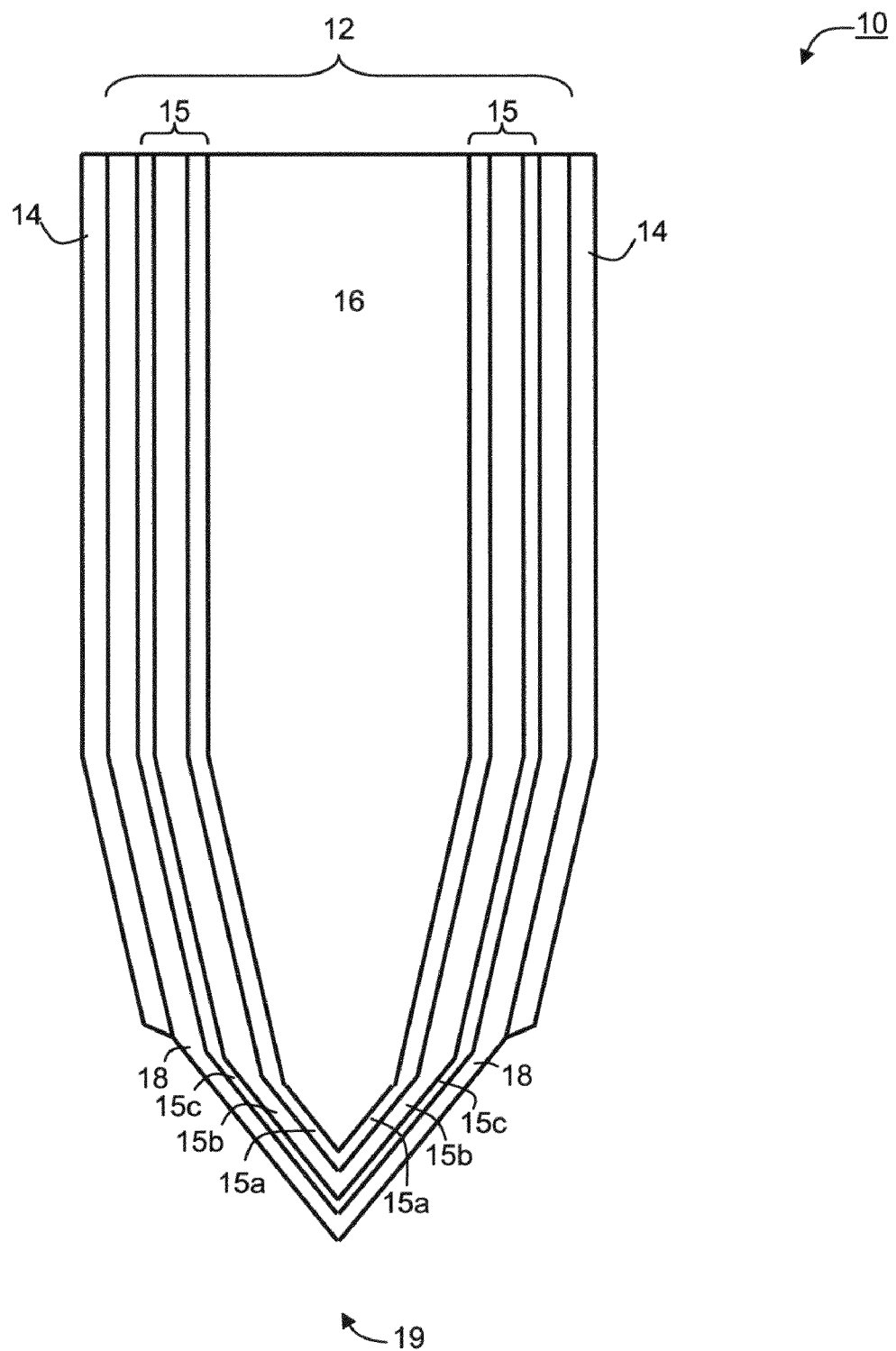
Figures 1F, 1G, 1H:
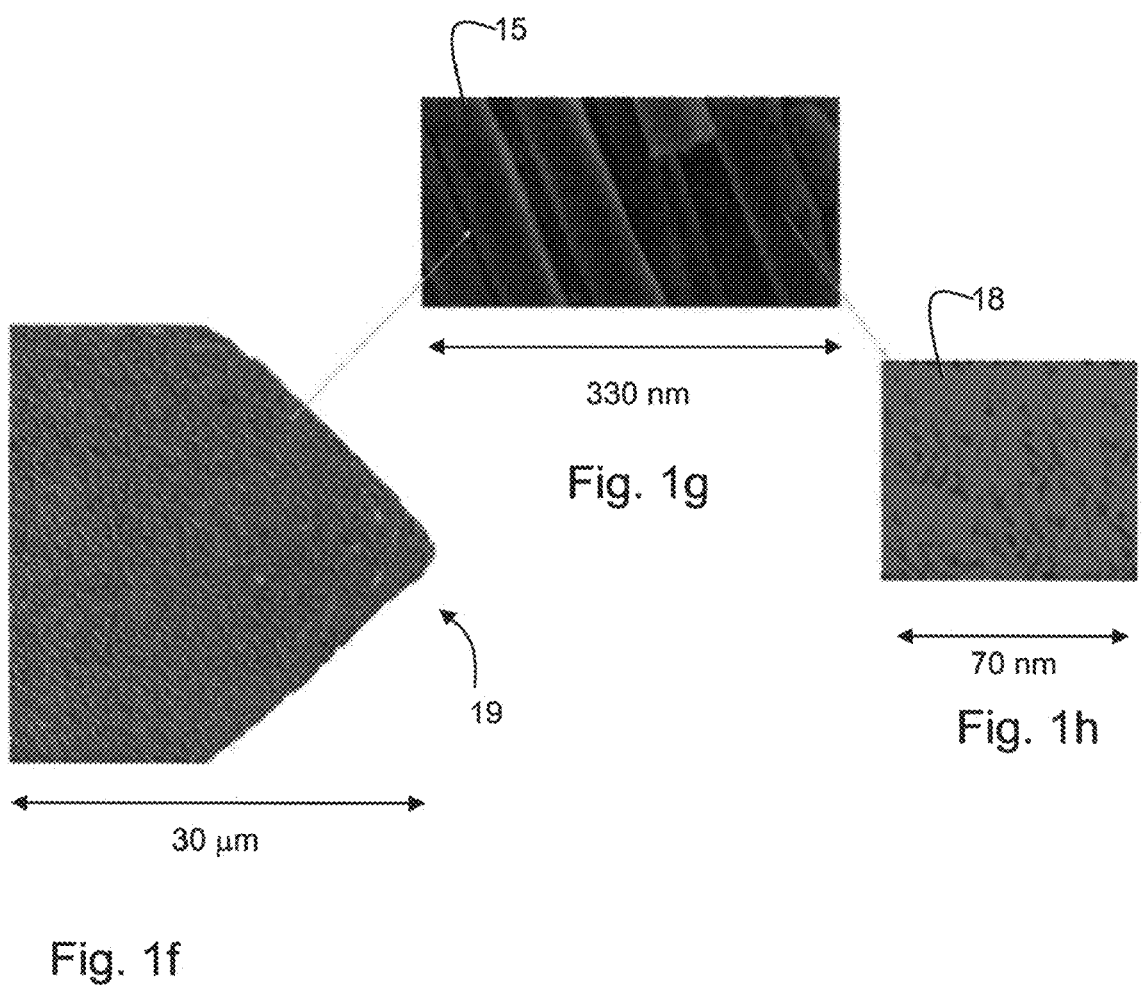
Figure 2A:
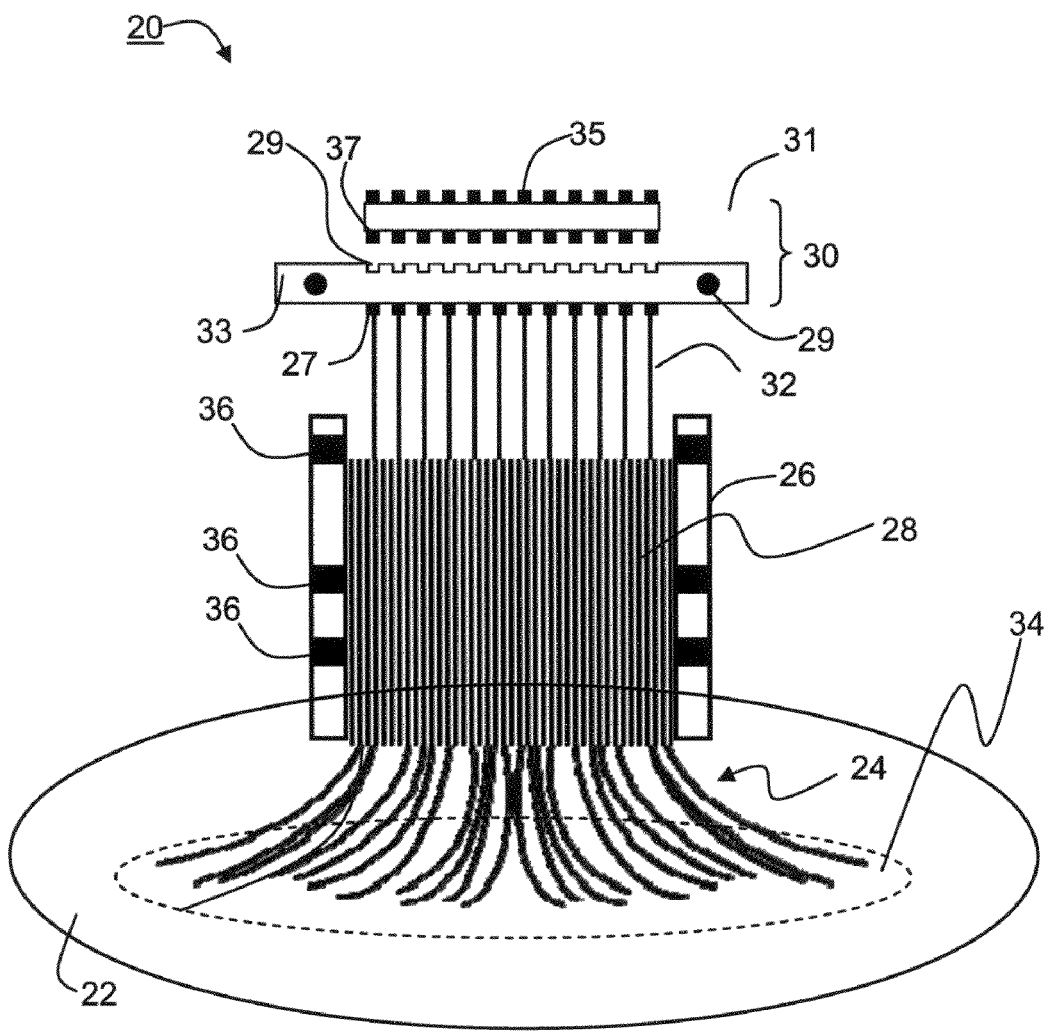
Figure 2B:
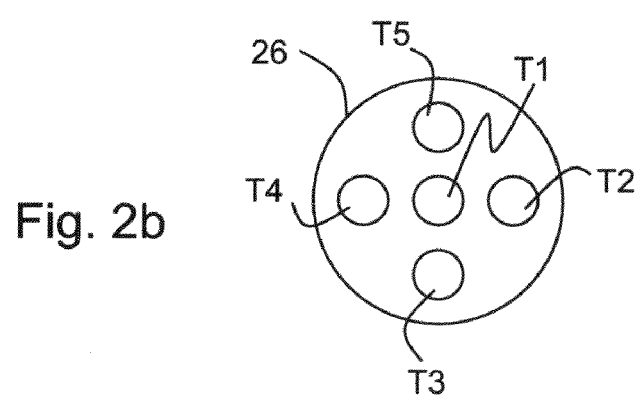
Figure 2C:
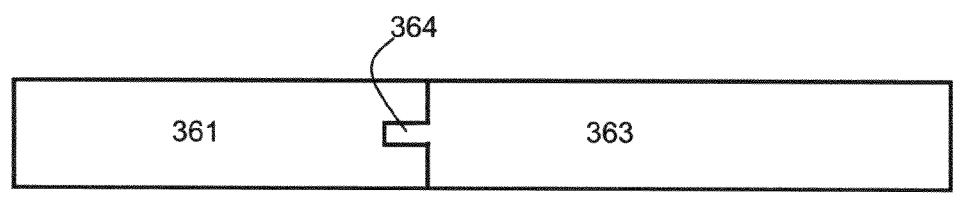
Figure 2D:
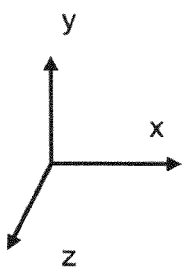
Figure 2D:
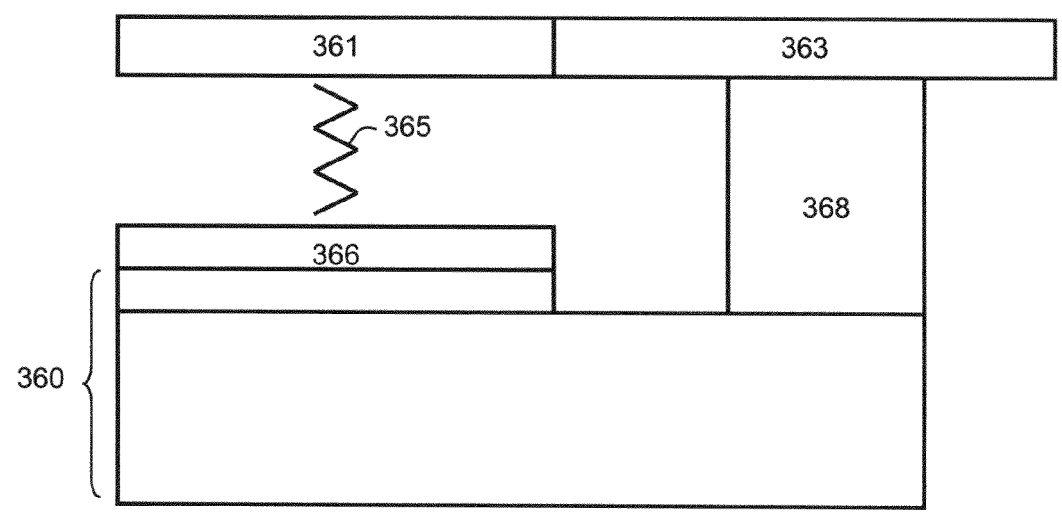
Figure 3:
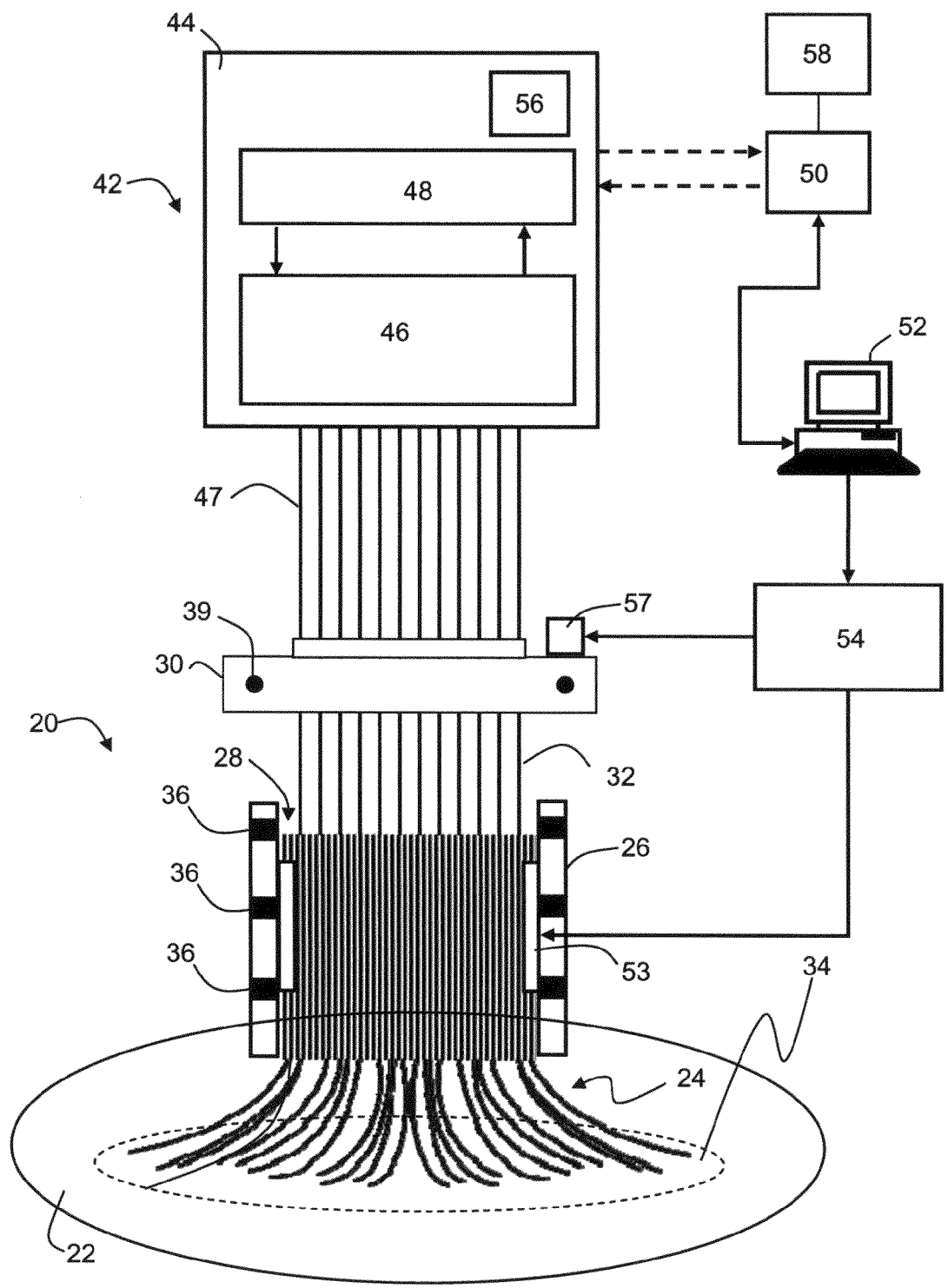
Figure 4:
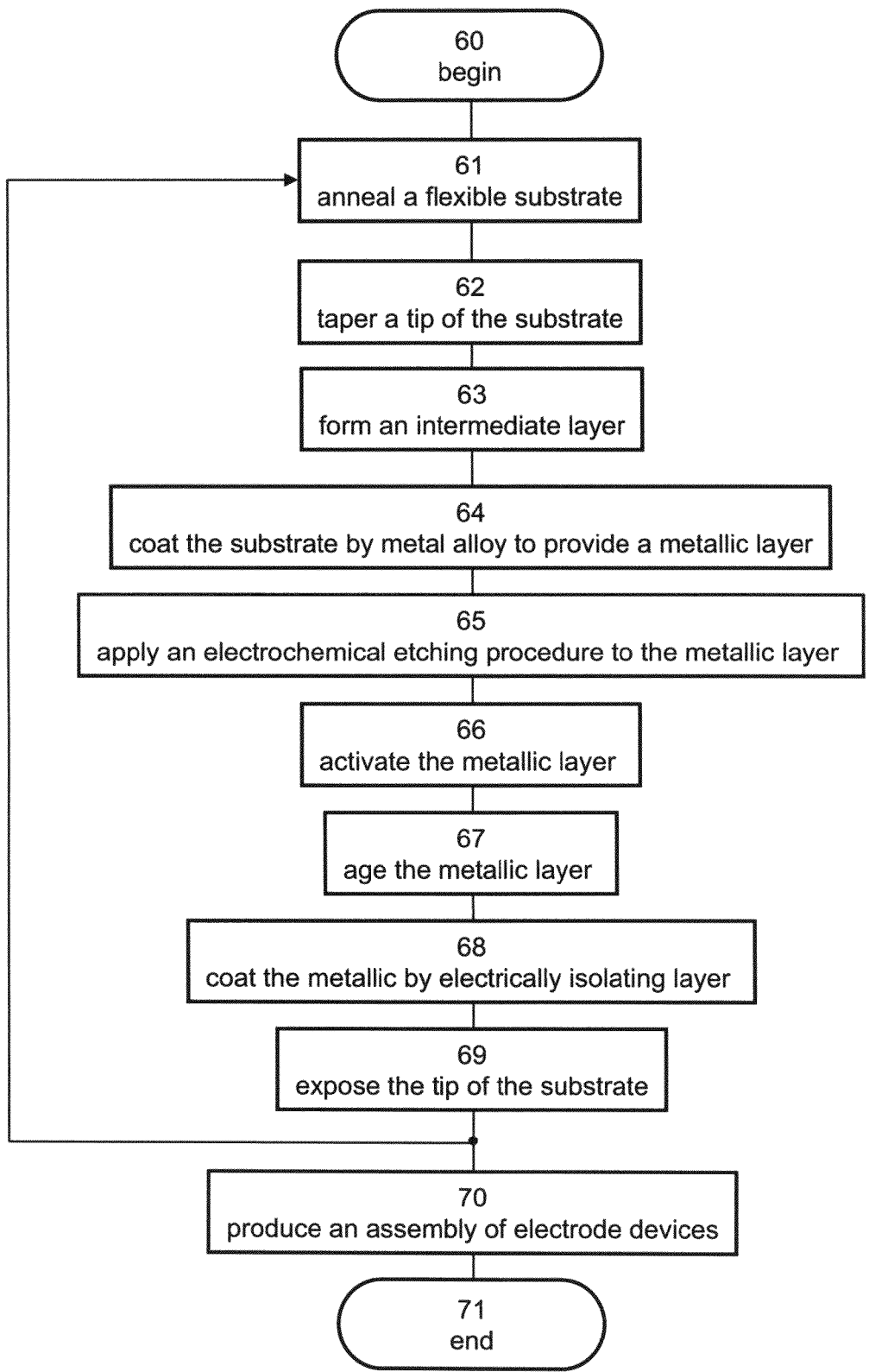
Figure 5:
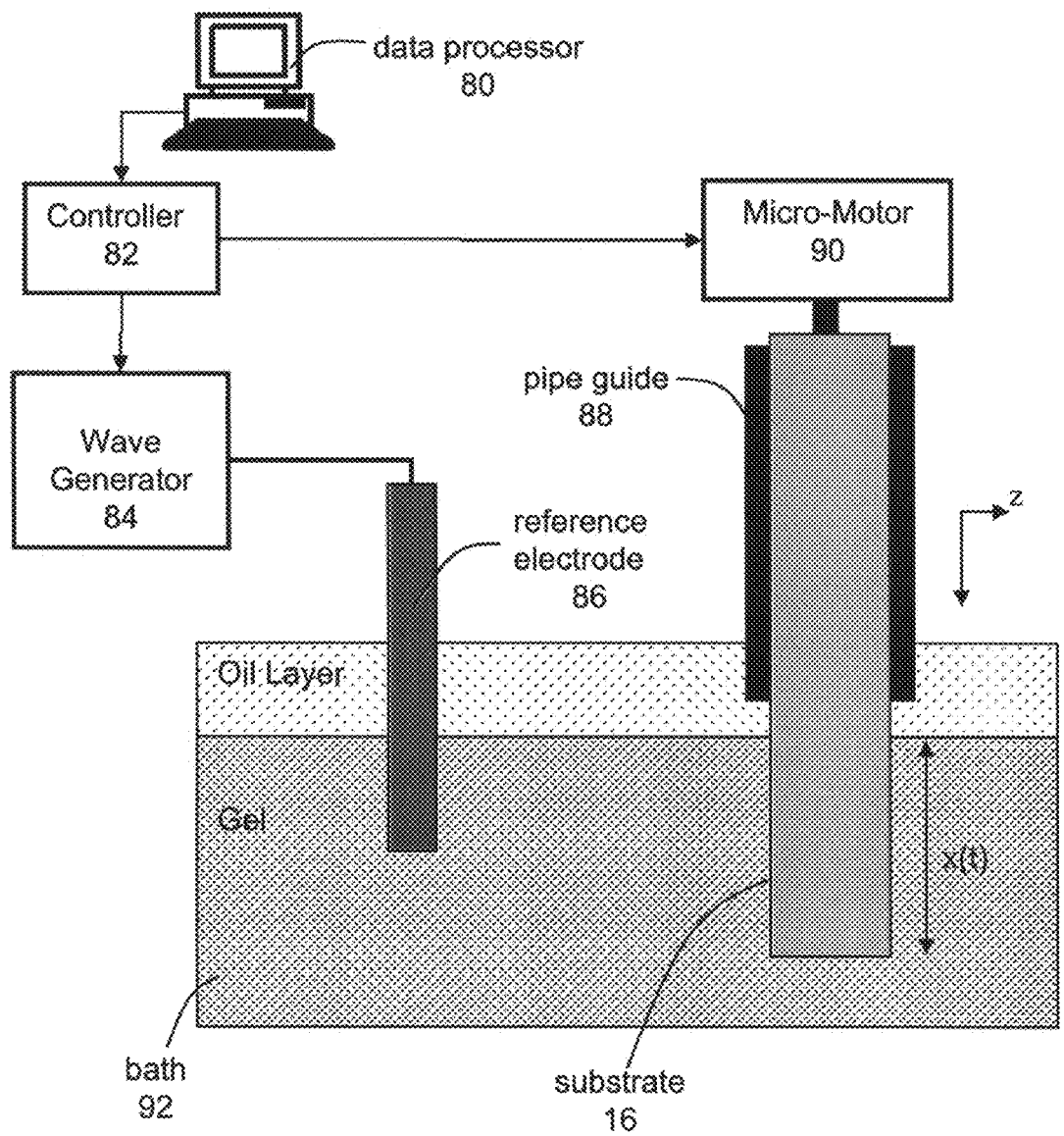
Figure 6:
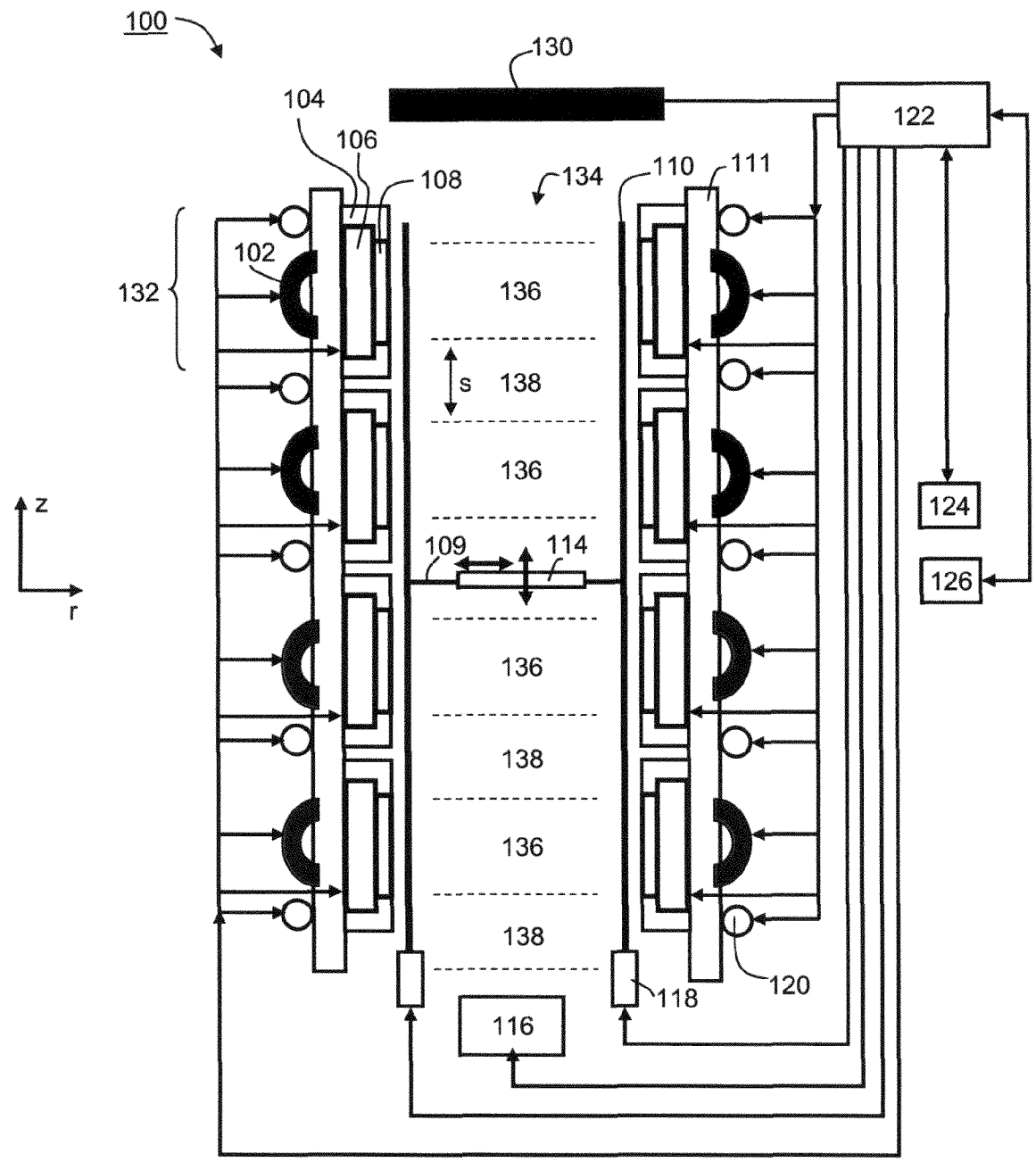

FIGS. 1a-b are schematic illustrations an electrode device, according to various exemplary embodiments of the present invention;

FIGS. 1c-d are magnified images of a 10 µm section (FIG. 1d) and a 100 nm section (FIG. 1c) of the electrode device, according to various exemplary embodiments of the present invention;

FIG. 1e is a schematic illustration of the electrode device, according to a preferred embodiment in which the electrode device comprises one or more intermediate layers;

FIGS. 1f-h are magnified images of a portion of the electrode device in a preferred embodiment in which the device comprises an intermediate layer formed of nanotubes;

FIG. 2a is a schematic illustration of an implantable stimulation device, according to various exemplary embodiments of the present invention;

FIG. 2b is schematic illustration of a top view of a guiding encapsulation in a preferred embodiment in which the guiding encapsulation comprises five trajectories;

FIGS. 2c-d are schematic illustrations of a microactuator, according to various exemplary embodiments of the present invention;

FIG. 3 is a schematic illustration of a system for delivery of electrical stimuli, according to various exemplary embodiments of the present invention;

FIG. 4 is a flowchart diagram of a method for manufacturing an electrode device, according to various exemplary embodiments of the present invention;

FIG. 5 is a schematic illustration of a system suitable for forming the tip of the electrode device, according to various exemplary embodiments of the present invention; and FIG. 6 is a schematic illustration of magnetron coating system for coating a substrate with one or more sputter materials, according to various exemplary embodiments of the present invention.

DESCRIPTION OF THE PREFERRED EMBODIMENTS

The present embodiments comprise a microelectrode device which can be used in various applications, including, without limitation, medical applications. Specifically, but not exclusively, the present embodiments can be used for deep brain stimulation, neuromonitoring, spinal stimulation, peripheral nerve stimulation, cardiac monitoring, cardiac rhythm management, ablation, mapping and the like. The present embodiments further comprise an electrode assembly, an implantable device and a system which incorporate the microelectrode device. Various exemplary embodiments of the invention comprise a method of manufacturing the electrode device and a method of implanting the implantable device.

The principles and operation of the method, system and device in accordance with preferred embodiments of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The performance of an electrode depends on its mechanical, electrical and physicochemical properties such as stiffness, charge transfer and charge storage. When the electrode is used in a biological environment such as in central nervous system the biocompatibility of the materials of the electrode also affect its performance. For example, for an electrode to be effective in stimulating neurons and/or sensing neurological activity in a neurological location, it is desirable to have a substantially stiff microelectrodes which is capable of penetrate the dura matter in straight direction to allow accurate positioning of the electrode.

The transfer of charge from an electrode to an ionic fluidic environment such as the extracellular liquid depends on the capacitance of the electrode as well as on heterogeneous charge-transfer reaction (also known as faradic reaction) and chemical changes occurring at the surface of the electrode. When an electrode is used for long-term stimulation within the ionic environment, irreversible chemical changes are inevitable, even when the electrode is composed of noble metals. The chemical changes may result in electrode malfunctioning and, more severely, to the release of toxic products. The problem is only aggravated at high current density.

Although attempts have been made to prevent faradic reaction using thin film coatings with low dielectric constant such as $TiO_2$ or $Ta_2O_5$, these attempts were not successful in applications in which high rate of charge transfer is required. Additionally, such coat results in an electrode device which consumes high rate of electrical power. In deep brain stimulation, for example, these devices have insufficient performances because they are incapable of providing the required charge transfer rate. Additionally, these devices are not suitable for long-term stimulation due to their high power consumption.

One electrode with reasonable electrical performance is an iridium oxide ($IrO_2$) electrode. $IrO_2$ films are produced by sputtering, activation of pure iridium or electroplating deposition techniques. These techniques, however, suffer from several limitations: $IrO_2$ electrodes manufactured by sputtering have poor electrical performance; the manufacturing of $IrO_2$ electrodes by activation is extremely expensive and is not practical for industrial production (several hundreds of U.S. dollars for a 10 cm long wire of pure iridium, 125 µm in diameter); and electroplating deposition of IrO2 on inexpensive substrate, such as tungsten is not effective, due to poor adhesion of the films.

Moreover, since $IrO_2$ films undergo faradic reaction, $IrO_2$ electrodes have low stimulation efficiency and low signal-to-noise ratio. When the $IrO_2$ electrode is used for long-term stimulation, its charge capacity and impedance are subjected to considerable changes which further reduce the stimulation efficiency and signal-to-noise ratio (SNR), even when the electrode is manufactured from pure iridium. Long term stimulation effects are more pronounced for very sharp tips of microelectrodes of high selectivity of stimulation.

Broadly speaking, capacitor non-faradic electrodes have relatively higher SNR compared to faradic electrodes, because in capacitor electrodes there is only a thermal noise which has no frequency dependence, while faradic electrodes possess, in addition to the incessant thermal noise, a frequency dependent shot noise. The spectrum of the shot noise characterizing the faradic electrodes depends on the charge transfer and mass transfer processes of electrolyte and species of the faradic reaction. An additional advantage of capacitor electrode is its relatively high stimulation efficiency. The stimulation efficiency is defined as the ratio between the current delivered to the target and the total current of the stimulus. Since faradic reactions consume current, they reduce the stimulation efficiency. Capacitor electrodes, on the other hand, are characterized by higher stimulation efficiency.

When an electrode is brought to a contact with a tissue, electrochemical reactions occurs at the electrode-tissue interface. This phenomenon is referred to as "polarization," and is known to significantly increase the interfacial impedance and, as a consequence, to reduce the effective charge transfer to and from the targeted tissue.

One method for reducing polarization effects is to increase the electrode surface area. However, a design trade-off exists in increasing the electrode size since in many applications, particularly medical applications, it is desired to have electrodes of small dimensions such that they can be easily implanted.

In a search for an electrode with improved mechanical, electrical and physicochemical properties, the Inventors of the present invention have devised a micrometric size electrode which can be used both for sensing and long term stimulation. As further detailed hereinunder, the electrode device of the present embodiments is characterized by an interfacial or active surface area which is substantially large for a micrometric structure.

The large surface area is realized by a novel nanometric pattern formed on the surface or a portion of the surface of the electrode device. The large surface area ensures that the electrode device of the present embodiments exhibits enhanced capacitance characteristic and, at the same time, diminishes or significantly reduces the effects of polarization. The enhanced capacitance characteristic makes the electrode device of the present embodiments suitable for efficient stimulation, because it is capable of carrying sufficient amount of electrical charge which can be transferred from the electrode device to the environment. The low polarization makes the electrode device suitable for sensing and recording electrical signals, because it allows the electrode device to accurately detect the signals with minimal or no distortion. The improved sensing performance of the electrode of the present embodiments facilitates sensing, recording and monitoring of action potentials with relatively low amplitudes.

An additional advantage of the large active surface area of the electrode device of the present embodiments is that it diminishes or reduces faradic reactions. This is because the extent of faradic reaction depends on the charge density at the interface between the electrode and the environmental fluid. In particular the faradic reaction is dominant at the conductor-insulator interface and near sharp edges. The large surface area of the electrode device of the present embodiments allows the electrode device to carry extremely high charge densities. It was found by the inventors of the present invention that the electrode device can carry a charge density which is more at least two orders higher than the charge densities of conventional $IrO_2$ films.

Referring now to the drawings, FIGS. 1a-b illustrates an electrode device 10, according to various exemplary embodiments of the present invention. Electrode device 10 comprises an electrically conductive core 12 coated by at least one electrically isolating layer 14. Conductive core 12 preferable has micrometric dimensions. A typical diameter D of core 12 is from about 1 µm to about 500 µm, e.g., about 50 µm. The typical length of electrode device 10 is from a few centimeters to a few tens of centimeters.

As used herein the term "about" refers to ±10%.

Conductive core 12 comprises a substrate 16 coated by one or more metallic layers 18 having a nanometric pattern thereon. The nanometric pattern is not shown in the illustrations of FIGS. 1a-b. FIGS. 1c-d are magnified images of a 10 µm section (FIG. 1c) and a 100 nm section (FIG. 1d) of layer 18. The images demonstrate the nanometric pattern on the surface of layer 18.

According to a preferred embodiment of the present invention the conductive core further comprises one or more intermediate layers which may or may not be metallic layers.

FIG. 1e is a schematic illustration of electrode device 10, in the embodiment in which conductive core 12 comprises one or more intermediate layers 15. Preferably, at least one of intermediate layer(s) 15 is electrically conductive. In the exemplified illustration shown in FIG. 1e, the intermediate layers 15 are interposed between substrate 16 and metallic layer 18. However, it is to be understood that it is not intended to limit the scope of the present invention to such configuration, and that each of intermediate layer(s) 15 can be interposed between substrate 16 and metallic layer(s) 18, between two adjacent layers of metallic layers 18, or between metallic layer(s) 18 and isolating layer 14. Representative examples of intermediate layers suitable for the present embodiments include, without limitation, a transition metal layer and a porous conductive polymer layer, e.g., a layer of nanotubes. The advantage of using transition metal layer is that such layer can increase the adhesion between, e.g., substrate 16 and metallic layer 18. The advantage of using porous conductive polymer is that it further increases the surface area of electrode device 10. Since there can be any number of intermediate layers, in various exemplary embodiments of the invention core 12 comprises at least one intermediate layer made of, at least in part, a transition metal, and at least one intermediate layer made of, at least in part, a porous conductive polymer. In the exemplified illustration of FIG. 1e, there are three intermediate layers, generally shown at 15a, 15b and 15c.

FIGS. 1f-h are magnified images of a portion of electrode device in the embodiment in which the device comprises an intermediate layer 15 formed of nanotubes. Shown in FIG. 1f are a 30 µm section of tip 19 (FIG. 1f), a 350 nm section of the nanotubes of layer 15 (FIG. 1g) and a 70 nm section of metallic layer 18 coating intermediate layer 15.

Conductive core 12 is at least partially exposed at a tip 19 of core 12. In various exemplary embodiments of the invention the electrically conductive core 12 is tapered. In other embodiments both core 12 and isolating layer(s) 18 are tapered. The tapering of core 12 is preferably achieved without attachment of additional bulk structures to electrode device 10. Specifically, although core 12 is formed of two or more layers, the tip of core 12 is preferably an integral part of the core, and is not attached thereto. Thus, according to a preferred embodiment of the present invention tip 19 is made of the same materials as core 12. This is a considerable improvement to electrodes which are assembled from different bulk materials, because it significantly enhances the mechanical properties, such as strength, stiffness and durability of the electrode device.

Electrode device 10 can be stiff or flexible, depending on the application for which electrode device 10 is designed. As further detailed hereinunder, the level of flexibility (or stiffness) can be controlled during the manufacturing of electrode device 10 by judicious selection of many parameters, including, without limitation, thicknesses, materials, coating technique and the like.

The nanometric pattern is preferably selected so as to ensure that the surface area (e.g., interfacial or active surface area) of core 12 is larger than its geometric surface area by at least one order of magnitude, more preferably by at least two orders of magnitude, most preferably by at least three orders of magnitude.

The interfacial or active surface area can be determined, for example, using a method developed by Brunauer, Emmett and Teller and commonly referred to as BET method. According to the BET method, the surface area is determined by allowing the surface to interact with nitrogen molecules and analyzing the corresponding adsorption curves. The BET method is well known in the art and is found in many publications. The geometric surface area of core 12 can be measured, for example, by obtaining an image of the electrode, approximating the geometrical shape of the electrode from the image, and, based on the geometrical shape, calculating the surface area from the image. For example, for right circular conical tip, the geometrical surface area can be the lateral area of the tip, $\pi R \sqrt{(R^2+L^2)}$, where R is the radius of the tip and L is its height.

For a tip having dimensions of about 15 µm in height, and about 10 µm in diameter, the typical interfacial surface area is from about 8 µm$^2$ to about 2000 µm$^2$, e.g., about 180 µm$^2$.

According to a preferred embodiment of the present invention metallic layer 18 of core 12 has a porous structure. The porous structure of metallic layer(s) 18 further increases the interfacial area of electrode device 10. Typically, the porosity of metallic layer(s) 18 is from about 40% to about 90%. According to a preferred embodiment of the present invention the average pore size of metallic layer(s) 18 is from about 5 nm to about 200 nm. In the embodiments in which core 12 also comprises an porous intermediate layer 15 (comprising, e.g., a porous conductive polymer), the average pore size of intermediate layer 15 is from about 10 nm to about 70 nm.

In experiments performed by the present Inventors it was found that the nanometric pattern of layer(s) 18 allows electrode device 10 to tolerate high charge density for a prolong period of time. Specifically, a surface charge density of more than 600 mC/cm$^2$ was maintained during continuous stimulation in saline solution at a frequency of 50 Hz for duration of several months. The calculation of charge density was obtained by dividing the overall charge by the geometrical area of the tip. The above performance is significantly better than the performance of an IrO$_2$ electrode reported by Cogan et al. (2004) in the Journal of Neuroscience Methods 137: 141-150. In this report the IrO$_2$ electrode was damage after few hours of continuous stimulation at charge density of 3 mC/cm$^2$.

The large surface area of core 12 is thus achieved by the coating of surface 16 by conductive layer(s) 18. In various exemplary embodiments of the invention the nanometric pattern of layer(s) 18 is selected so as to ensure that the surface area of core 12 is larger than the surface area of substrate 16 by at least one, more preferably at least two, most preferably at least three orders of magnitude. A preferred technique for providing one or more conductive layers on substrate 16 is provided hereinunder.

It will be appreciated that the larger the interfacial surface area of core 12 the higher is the sensitivity of electrode device 10 to low amplitude signals. The nanometric pattern of layer(s) 18 significantly reduces the polarization of electrode device 10. It was found by the Inventors of the present invention that the polarization of electrode device 10 is lower than the polarization of platinum electrodes by at least two orders of magnitude. This allows sensing electrical signals with high SNR. For example, it is recognized that during the targeting step of DBS, action potential activity is typically recorded at a SNR of about 100. Without bounding to any theory, it is postulated that the improvement in SNR of electrode device 10 of the present embodiments is proportional to the increment in its interfacial surface area. According to a preferred embodiment of the present invention electrode device 10 is capable of sensing electrical signals at an SNR of at least 300, more preferably at least 400, more preferably at least 500, even more preferably, but not obligatorily, at least 1000.

According to a preferred embodiment of the present invention layer 18 is capable of preventing penetration of macromolecules therethrough. In experiments performed by the present inventors it was found that layer 18 allow penetration of small electrolytes such as Na$^+$ and Cl$^-$ with partition coefficient close to unity. On the other hand, large macromolecules such as proteins were excluded. This is particularly advantageous when electrode device 10 is used for stimulation in biological environment. Since the adsorption of macromolecules on layer 18 is negligible, complications, such as gliosis, are prevented or minimized.

Substrate 16 of core 12 can be made of any conducting material, such as, but not limited to, a conductive metal (e.g., stainless steel, tungsten, platinum, platinum-iridium, titanium, etc.), a conductive polymer (e.g., a carbon fiber), and the like. A conductive polymer substrate is preferred for small cores (below about 20 µm), while a metal is preferred for cores of larger diameter (above 20 µm).

According to a preferred embodiment of the present invention metallic layer(s) 18 comprise a metal alloy nitride compound. The metal alloy preferably comprises at least two metals each can be a transition metal, a rare earth metal or an alkali metal. For example, the metal alloy can comprises a noble metal, such as, but not limited to, Pt, Pd, Rh, Re, Au and Ir. Alternatively or additionally, the metal alloy can comprise a metal which is capable of producing a stable oxide element, such as, but not limited to, $TiO_2$, $Ta_2O_5$, NiO, $Al_2O_3$, IrO, $IrO_2$ and $IrO_3$. Further, the metal alloy can comprise a reactive metal, including, without limitation, Mo and W.

The metal alloy nitride compound can be written as the chemical formula $Pt_{y1}Pd_{y2}Rh_{y3}Re_{y4}Au_{y5}Ir_{y6}Ti_{y7}Ta_{y8}Ni_{y9}Al_{y10}W_{y11}Mo_{y12}Ny_{13}$, where $y_1, y_2, y_3, y_4, y_5, y_6, y_7, y_8, y_9, y_{10}, y_{11}, y_{12}$ and $y_{13}$ are the contents of each element in the compound, and can represent any percentage from 0% to 100%.

The intermediate layer (in the embodiment in which the conductive core comprises one or more intermediate layers), can comprise a transition metal layer which is preferably selected to increase the adhesion of the substrate and the metal alloy nitride compounds. Also contemplated, as an alternative to the aforementioned transition metal layer or in addition thereto, are one or more intermediate layers which comprise a porous conductive polymer of sufficiently high surface to volume ratio. Such layer can be made, at least in part of metal nanotubes and/or carbon nanotubes. Carbon nanotubes are widely used in the art of nanofabrication. Two major forms of carbon nanotubes exist, single-walled nanotubes (SWNT), which can be considered as long wrapped graphene sheets and multi walled nanotubes (MWNT) which can be considered as a collection of concentric SWNTs with different diameters. Also known are armchair bundles of metallic carbon nanotubes, all of which are contemplated to be used in intermediate layers 15.

SWNTs have a typical length to diameter ratio of about 1000 and as such are typically considered nearly one-dimensional. These nanotubes consist of two separate regions with different physical and chemical properties. A first such region is the side wall of the tube and a second region is the end cap of the tube. The end cap structure is similar to a derived from smaller fullerene, such as $C_{60}$.

The main technical problem in such nanotube-based electrode devices is the high energy barrier (the Schottky barrier) which is present at the interface between metallic layers and nanotube layers, and which hinders the passage of electron from the metallic layer to the nanotube layer. The present inventors uncovered a solution to the Schottky barrier problem, by interposing the nanotube layer between two atomic layers which enhance the electronic coupling between the nanotube layer and its adjacent metallic layers.

Titanium, nickel and palladium are known to form continuous and quasi-continuous coating, while gold, aluminum and iron form only discrete particles on the SWNT surface. A particularly advantageous material is palladium which consistently yields contacts with low contact resistance to both metallic and semiconducting nanotubes [Javey et al., 2003, Nature 424:654; Mann et al., 2003, Nano Lett. 3:1541; Chen et al., 2005, Nano Lett. 5:1497]. Platinum, on the other hand, forms poor contacts to both metallic and semiconducting SWNTs.

Thus, for example, in the embodiment illustrated in FIG. 1e, intermediate layers 15 comprise one or more atomic palladium layers 15a coating substrate 16, one or more nanotubes layers 15b coating atomic layers 15a, and one or more additional atomic palladium layers 15c coating nanotubes layer(s) 15b.

Metallic layer(s) 18 can be a single layer or a plurality of layers, as desired. According to a preferred embodiment of the present invention layer 18 comprises at least one intermediate metallic layer and at least one superficial metallic layer. A schematic illustration of an intermediate metallic layer 18a and a superficial layer 18b is shown in FIG. 1b. Intermediate metallic layer 18a can be made of, for example, gold and superficial layer 18b can comprise, for example, $IrO_2$, or, more preferably, the aforementioned metal alloy nitride compound. This embodiment is particularly useful when substrate 16 is made of tungsten. When substrate 16 is made of stainless steel the preferred intermediate metallic layer 18a is platinum. In this embodiment, superficial layer 18b can also comprise $IrO_2$ or metal alloy nitride compound.

Isolating layer 14 preferably comprises a biocompatible material, so as to enable the use of electrode device 10 in medical applications such as, but not limited to, chronic implantation, e.g., for deep brain stimulation. Representative examples for suitable biocompatible materials to be used in layer 14 include, without limitation, Parylene™ (e.g., Parylene-C™), and Polyimide which have been proven to be effective biocompatible insulation materials with enhanced mechanical properties and low water vapor transmission. Parylene-C is poly-para-xylylene modified by substituting a chlorine atom for one of the aromatic hydrogens.

The thickness of layer 14 depends on the diameter of substrate 16. Specifically, for substrate diameter of about 200-300 μm, the thickness of layer 14 is preferably about 10 μm; for substrate diameter of about 100-200 μm (e.g., about 125 μm), the thickness of layer 14 is preferably about 5-6 μm; for substrate diameters 30-100 μm (e.g., about 50 μm) the thickness of layer 14 is preferably about 3-4 microns; and for substrate of smaller diameter (below 30 μm, e.g., about 25 μm) the thickness of layer 14 is preferably about 2-3 μm.

Alternatively, isolating layer 14 can comprise or an inorganic material, such as, but not limited to, glass or quartz. In this embodiment, the thickness of layer 14 is preferably from several microns to several hundreds of microns.

A preferred technique for depositing layer 14 on coat 12 is provided hereinunder.

The enhanced mechanical, electrical and electrochemical properties of electrode device 10 make the device suitable for various medical applications which require accurate sensing and/or stimulation. Whether serving in a stimulation capacity or a sensing capacity, electrode device 10 can be implanted in various locations, including, without limitation, in the brain, along peripheral nerves, within the epidural or the intrathecal spaces of the spinal column, about the heart and intravenously. Implanted in such implantation locations, electrode device 10 can be used for deep brain stimulation, neuromonitoring, spinal stimulation, peripheral nerve stimulation, cardiac monitoring, cardiac rhythm management, ablation, mapping and the like. Thus, electrode device 10 can be used to treat many disorders including, without limitation, chronic pain, symptoms of Parkinson's disease, epilepsy, hearing disorders, depression, eating disorders (e.g., anorexia), schizophrenia, muscle disorders, arrhythmia and the like.

In at least a few of these applications, the desired treatment area is small and proximate to other tissue for which stimulation would produce undesirable effects. This is especially the case in deep brain stimulation where neural tissue is tightly packed. The nerves in any one region may be responsible for a plethora of functions. For example, excess stimulation in the sub-thalamic region of the brain could lead to paresthesia about the head, loss of balance, depression, peresis, dysarthia or dystonia. The ability of the electrode device of the present embodiments to perform both stimulation and sensing allows accurate treatment to a predetermined region or even a tortuous path in order to achieve a desired effect. The electrode device of the present embodiments is advantageous because it substantially avoids stimulating the surround tissue hence minimize or prevent undesired effects.

While the electrode device of the present embodiments is useful as a single microelectrode, in many applications it is desired to employ one or more bundles of microelectrodes. Thus, according to another aspect of the present invention there is provided an electrode assembly, comprising at least one bundle of electrode devices, where the principles and operations of each electrode device is similar to the principles and operations of electrode device 10 described hereinabove.

As stated, electrode device 10 can have any level of flexibility or stiffness. For medical applications in which it is required to accurately apply stimulations, the electrode assembly is preferably comprise one or more bundles of flexible electrodes which can fan outward and cover a three-dimensional region. Each electrode device or cluster of electrode devices within the bundle can be addressed separately and can therefore apply a stimulation with different characteristics (amplitude, frequency, phase, pulse shape), depending on the tissue contacting the respective electrode device or cluster of electrode devices. In various exemplary embodiments of the invention the electrode devices in the electrode assembly are of different diameters, so as to facilitate application of different stimulation characteristics. Electrode devices contacting surround tissue where it is desired not to apply stimulation can be "switched off". Namely no stimulation signals are transmitted to such electrode devices. The process can be performed in real time such that location of each electrode device or cluster of electrode devices within the bundle is assessed continuously or at a predetermined timing protocol, and the decision whether or not to transmit stimulation signals (and the characteristic of the stimulation, if applied) is based on the assessed location and the electrical activity of the target.

For example, when the electrode assembly is used in DBS for treating syndromes of Parkinson's disease, stimulations are performed only when the hyperactivity of tremor cell is detected, so as to block the tremor event. When the activity return to the normal level, the stimulations can be ceased. Such protocol is advantageous both because it reduces side effects due to uncontrolled continuous stimulation, because it reduces power consumption.

Reference is now made to FIG. 2a, which is a schematic illustration of an implantable stimulation device 20 for delivery of electrical stimuli to a neurological location 22. Neurological location 22 can be any location in the body having neurons therein, e.g., the brain, the spinal cord and the like.

Representative examples of neurological locations include, without limitation, globus pallidus internus (GPi), including globus pallidus internus internal segment (Gpi,i) and globus pallidus internus external segment (Gpi,e), globus pallidus externus (Gpe), ventral medial (Vim) thalamic nucleus, other portion of the thalamus, subthalamic nucleus (STN), caudate, putamen, other basal ganglia components, cingulate gyrus, other subcortical nuclei, nucleus locus ceruleus, pedunculopontine nuclei of the recitcular formation, red nucleus, substantia nigra, other brainstem structure, cerebellum, internal capsule, external capsule, corticospinal tract, pyramidal tract, ansa lenticularis, white matter tract, motor cortex, premotor cortex, supplementary motor cortex, other motor cortical regions, somatosensory cortex, other sensory cortical regions, Broca's area, Wernicke's area, other cortical regions, other central nervous system structure, other peripheral nervous system structure and other neural structures.

In various exemplary embodiments of the invention device 20 comprises an electrode assembly 24 as described above, disposed in a guiding encapsulation 26. Guiding encapsulation 26 can comprise a single trajectory or several trajectories, as desired. FIG. 2b schematically illustrates a top view of encapsulation 26 in a preferred embodiment in which encapsulation 26 comprise five trajectories T1, T2, T3, T4 and T5. The typical distance between adjacent trajectories is about 2 mm center to center.

Device 20 further comprises a plurality of microwires 28, connected to assembly 24 such that electrical communication is established in an addressable manner between each microwire and at least one of the electrode devices in assembly 24. The electrical communication is addressable in the sense that each electrode device or cluster of electrode devices can receive and transmit signals via the respective microwire independently of other electrode device or cluster of electrode devices in assembly 24. For example, when there are N microwires and N electrode devices, each microwire can communicates with one and only electrode device, independently with the communication of other microwires with other electrode devices. Yet, each electrode can be perform an action (e.g., stimulation) based on recorded activity from the other electrodes in the array.

Microwires 28 can be of any type known in the art, provided they are capable of transmitting electrical signals and that they are connectable to the electrode devices in addressable manner. Each microwire can be similar to electrode device 10, but since microwires 28 are not intended to directly contact the tissue in location 22, some of their features can be different. For example, there is no need for the microwires to have a tapered structure, a metallic layer coating the conductive substrate, or a nanometric pattern, although such features are not excluded from the scope of the present invention. Preferably, microwires 28 are stiff microwires.

According to a preferred embodiment of the present invention assembly 24 is disposed in guiding encapsulation 26 in a manner such that when a pressure is applied on microwires 28, the flexible electrode devices fan outward from encapsulation 26 to define a target region, generally shown at 34, which is substantially larger than a cross-sectional area of encapsulation 26. The fanning out of the electrode device is accomplished due to elastic forces present between adjacent electrode devices.

According to a preferred embodiment of the present invention guiding encapsulation is designed and constructed such that it can be removed once assembly 24 fans outwards from encapsulation 26. Preferably encapsulation 26 is formed of a plurality of disconnectable parts to facilitate such removal. The removal of encapsulation 26 is preferably accomplished by means of one or more microactuators 36 mounted on or formed in encapsulation 26.

Reference is now made to FIGS. 2c-d which are schematic illustrations of a top view (FIG. 2c) and a front view (FIG. 2d) of microactuator 36, according to various exemplary embodiments of the present invention. Microactuator 36 preferably comprises a movable or rotating plate 361 and a fixed plate 363 on a via 368. Plates 361 and 363 are preferably connected by a shaft-groove arrangement 364. Displacement of movable plate 361 is actuated by a spring 365 connecting plate 361 with a gate 366 of CMOS double layer capacitor 360. The extent of displacement depends on the applied voltage of the gate. Once bias is applied to capacitor 360, plate 361 detaches from plate 363.

The removal of encapsulation 26 allows electrode assembly 24 to "float" within target region 34. This is particularly useful for dynamic target regions, such as the brain which is oftentimes subjected to small displacement following, e.g., head motions. The floating of electrode assembly 24 within target region 34 ensures that the position of each electrode device or cluster of electrode devices in assembly 24 is substantially stable relative to the position of its target tissue. This is a major advantage to, e.g., the rigid macroelectrode of Medronix™, which is oftentimes displaced from its designated location.

Referring again to FIG. 2a, in various exemplary embodiments of the invention device 20 comprises a multi-channel connector 30, configured to establish multi-channel communication with bundle 24 via microwires 28. Connector 30 is preferably a solid state connector and it can communicate with microwires 28 via a plurality of flexible microwires 32. When connector 30 is a solid state connector, such as a silicon device, it is preferably comprises two parts, 31 and 33 each having two facets. Part 31 of connector 30 comprises, on one facet, a plurality of micro connectors 35 designed connectable to a plurality of wires (not shown see 47 in FIG. 3) which transmit signal to and from device 20, and on the other facet, a plurality of micro vias 37. Part 33 comprises, on one facet, a plurality of micro grooves 29, sizewise compatible with vias 37, and on the other facet, a plurality of micro connectors 27 designed connectable to microwires 32. Part 31 and 33 are thus connectable in male-female configuration whereby vias 37 engage grooves 29. Note that 20 float in the brain due to the flexible wires 32.

Connecter 30 can be mounted on an external organ (e.g., an external organ having a hard tissue, such as the skull) near neurological location 22 by a mounting mechanism, e.g., miniature screws 39. Alternatively, connector 30 can be connected to an internal organ (e.g., an internal organ having a soft tissue, such as the brain tissue) near neurological location 22.

In use, device 20 is implanted at or near the neurological location 22, and assembly 24 is brought to a contact with the neurons therein, by applying pressure on microwires 28. The pressure is preferably applied on connector 30 such that wires 32 are pushed downward within encapsulation 26 and apply pressure on wires 28. To facilitate the procedure, microwires 32 can be coated by a coat of biodegradable material which makes the microwires stiff and enhances the transmission of pressure therethrough. Connector 30 is then mounted to an external organ, which can be near location 22. When device is used for DBS, connector 30 can be mounted on the skull. In various exemplary embodiments of the invention encapsulation 26 is removed, e.g., by disassembling it, and microwires 32 contact the body fluids, such that the coat is degraded and microwires 32 become flexible.

Signals sensed by the electrode devices are transmitted through microwires 28 to a remote location (not shown, see FIG. 3), where they are analyzed to determine the location of each electrode device or cluster of electrode devices. Based on the location, stimulation signals are transmitted in addressable manner to assembly 24 via microwires 28. Device 20 thus provides selective and high resolution stimulation to location 22.

The inclusion of the electrode assembly of the present embodiments in device 20 significantly reduces the complexity of the procedure with one or, at most, two trajectories. Thus, referring to FIG. 2b, the electrode assembly is inserted into the central trajectory T1, and the precise target location is determined without testing any other trajectory. This is because the electrode devices in the assembly fan out of the encapsulation and define a target region which is larger than the trajectory. The signal sensed by the electrode assembly can be used to provide a map of electrical field intensity. This map is sufficient for determining the best trajectory for implantation, because the electrode devices cover the area of T1 as well as cardinal sections of each adjacent trajectory. The best trajectory for implantation can be determined by the coordinate of the electrode device or cluster of electrode devices of the highest electrical field intensity. For example, suppose that the map reveals that trajectory T1, in which the electrode assembly is initially inserted, is off-center relative to location at which the stimulation is to be performed. The map also reveals, without having to perform another recording test, to which of the four directions (T2-T4) the electrode assembly is to be shifted. The surgeon then places the electrode assembly at the corresponding trajectory for implantation. An additional advantage of the electrode assembly of the present embodiments is that it can tolerate high current densities and there is no need to replace the electrode during targeting.

The above procedure is a significant improvement to conventional implanting process. For example, in conventional DBS five trajectories are typically needed for precise determination of the coordinate of the target. For accurate targeting using conventional test microelectrode, the surgeon needs to test each and every trajectory until he decides that the test microelectrode is properly positioned. Several replacements of the microelectrodes are required during the procedure. Once recordings are made in all the trajectories, the surgeon introduces the macroelectrode into the best trajectory. The electrode assembly of the present embodiments, as stated, requires a single trajectory for targeting and, at most, one additional trajectory for implantation.

Reference is now made to FIG. 3 which is a schematic illustration of a system 40 for delivery of electrical stimuli to neurological location, according to various exemplary embodiments of the present invention. System 20 comprises the implantable device 20, for applying the stimulation to the neurons in location 22 as further detailed herein above. System 20 further comprises a second implantable device 42, which comprises a device body 44 having therein a multi-channel system 46 capable of providing stimulation signals to device 20 and receiving sensing signals from device 20. The communication between device 20 and device 42 is preferably via a plurality of flexible microwires 47. Second device 42 can be implanted in a convenient location, e.g., the chest or the like.

Multi-channel system 46 provides stimulation signals to device 20 substantially in real time based on sensing signals sensed by the electrode assembly 24 of device 20 and using a stimulation protocol. The second implantable device 42 comprises a memory medium 48 which communicates with multi-channel system 46 and configured to store, at least temporarily, the stimulation protocol and/or the sensing signals. In various exemplary embodiments of the invention system 20 further comprises a wireless communication system 50 for establishing communication between memory medium 48 and an external data processor 52.

Data processor 52 is preferably supplemented by an algorithm which calculates the stimulation protocol based on the sensing signals sensed by electrode assembly 24. The stimulation protocol is transmitted by data processor 52 via wireless communication system 50 to be stored in memory medium 48. The algorithm preferably maps the signals sensed by electrode assembly 24 to provide a neurological activity map of target region 34. The neurological activity map is the used for calculating the stimulation protocol. For example, regions in the neurological activity map which are associated with surround tissue which is not to be stimulated, are marked by the algorithm as such and no stimulation signals are written in the stimulation protocol for electrode devices contacting these regions. Similarly, for regions in the neurological activity map which are associated with neurons which are to be stimulated, the algorithm writes to the protocol stimulation signals to be transmitted to the respective electrode devices. The algorithm can also designate specific stimulation characteristics for each stimulation signal.

The system of the present embodiments is capable of providing progressive and smart long-term treatment. In various exemplary embodiments of the invention the multi-channel system 46 performs real time and high resolution recording of neural activity and the memory medium 48 stores the data or samples thereof. The advantage of using multi-channel system 46 is that it allows stimulation of the target region in a spatial-selective and temporal-selective manner. Thus, according to a preferred embodiment of the present invention multi-channel system 46 uses the stimulation protocol stored in memory medium 48 stores and signals device 20 to perform stimulation only at specific intervals of times and only at specific locations within target region 34. For example, when system 40 is used for treating Parkinson's disease, the stimulation is performed only when hyperactivity of neurons is detected and only in the location at which the hyperactive neurons are located. Performing stimulation in specific time intervals and specific locations minimizes the side effects of stimulation. Additionally, the progress of the treatment and/or the disease can be performed based on the real time sensing signals which are recorded and stored in memory medium 48.

System 40 is advantageous over many conventional systems, such as, for example, the stimulating system of Medtronic Inc. (see, e.g., U.S. Pat. Nos. 5,713,923, 5,716, 377, 5,800,474, 5,833,709, 5,843,148, 5,978,702, 6,038,480, 6,227,203, 6,253,109, 6,353,762, 6,374,140, 6,473,653, 6,671,555, 6,980,863, 7,006,872, 7,035,690). This system comprises a low impedance macroelectrode which is not capable of recording neural activity. Medtronic's system is a one channel system which employs a fixed stimulation protocol to perform continuous, low resolution, stimulation using the macroelectrode. The stimulation protocol does not taking into consideration the changes, interrupt and decay in the activity of the tremor cells. Since the activity of tremor cell can be normal in certain time-intervals, there is a danger that stimulation at these time-intervals will be destructive and will lead to undesired side effects and complication. Unlike Medtronic's system, the system of the present embodiments performs selective stimulation as described hereinabove, such that the amount of side effects is significantly reduced.

According to a preferred embodiment of the present invention system 40 comprises a mechanism 54 for controlling the pressure applied to microwires 28 for extrude assembly 24 outward from encapsulation 26. Mechanism 54 can be a nano drive motor, controlled by data processor 52. Nano drive motors for advancing microelectrodes into specific location in a precise manner are known in the art and found in various patents and patent application, see, e.g., U.S. Pat. No. 6,567, 690. Mechanism 54 can also comprises two or more synchronized nano drive motors. For example, a first nano drive motor 53 mounted on the inner face of encapsulation 26 for establishing motion of wires 28, and a second first nano drive motor 57 for applying pressure on connector 30.

Second device 42 can be powered by a rechargeable power source 56, in which case system 40 preferably comprises a recharging device 58 which can remotely recharge power source 56 via wireless communication system 50.

The ability of system 40 to advance the electrode devices to a precise location in target region 34, to sense electrical activity, and to selectively stimulate the neurons, makes it optimal candidate to be used in deep brain stimulation.

It has shown that the STN consisted of a regional compartmentalization of neurons with different receptive fields and electrophysiological properties [Abosch et al., 2002, J. Neurosurg 97:1167-1172]. As stated in the Background section above, low resolution stimulation using microelectrodes are known to generate contradictory responses in different zones of the STN, which inhibition and/or decreased activity in the stimulated nucleus and increase in activity for the efferent nuclei of the stimulated nucleus. These results support the need for the system of the present embodiments which can provide selective stimulation with high resolution. Theoretical studies showed that nondestructive specific stimulation with high resolution can minimized activation effects caused due to uncontrolled electrical field feedbacks [Cameron et al., 2004, J. Neurophysiol 91:1457-1469]. It is therefore assumed that the high resolution stimulation of the present embodiments can expand the treatment to many symptoms of Parkinson diseases, i.e., symptoms other than tremor.

Being performed by a single system, the selective stimulation and recording of the present embodiments provides efficient blocking and controlling of malfunction of neural network activity, functions, pathways of control and interactions.

Reference is now made to FIG. 4 which is a flowchart diagram of a method for manufacturing an electrode device, according to various exemplary embodiments of the present invention.

It is to be understood that, unless otherwise defined, the method steps described hereinbelow can be executed either contemporaneously or sequentially in many combinations or orders of execution. Specifically, the ordering of the flowchart of FIG. 4 is not to be considered as limiting. For example, two or more method steps, appearing in the following description or in the flowchart of FIG. 4 in a particular order, can be executed in a different order (e.g., a reverse order) or substantially contemporaneously. Additionally, one or more method steps appearing in the following description or in the flowchart of FIG. 4 are optional and are presented in the cause of providing what is believed to be a useful and readily understood description of an embodiment of the invention. In this regard, there is no intention to limit the scope of the present invention to the method steps presented in FIG. 4.

The method begins at step 60 and, optionally and preferably, continues to step 61 in which a flexible substrate of micrometric size is subjected to an annealing process. The substrate can be, for example, a flexible wire of metal or a conductive polymer. The annealing process is performed to provide sufficient stiffness to the substrate, depending on the application for which the electrode device is designed. The annealing is preferably performed by subjecting the wire to a heating DC current and a tension force at the same time. The magnitude of the tension force, F, and the DC current, I, depends on the diameter, D, and length, L, of the wires. For example, for a wire of 10% Pt—Ir with L=15 cm and D=125 µm, the preferred annealing parameters are current of about 1.4 A and tension force of about 3.63 Newtons. For the same wire with D=50 µm, the preferred current is about 0.5 A and the preferred force is about 0.76 Newtons.

In various exemplary embodiments of the invention the method continues to step 62 in which the substrate is tapered to form a tip. The tip formation is preferably performed by a computer controlled chemical etching process.

A preferred system for forming the tip is schematically illustrated in FIG. 5. The substrate 16 is connected to micromotor 90 which gradually dips it into a bath 92 filled with etching solution. A reference electrode 86 is statically dipped into the solution and being applied with electrical current at predetermined (not necessarily constant) frequency and magnitude. Reference electrode 86 receives signals from a wave generator 84. Wave generator 84 and micro-motor 90 are controlled by a controller 82 which is connected to a data processor 80.

Preferred solution for tungsten substrate is a mixture of KOH and $NaNO_2$ or a mixture of NaOH and NaCN. Preferred solution for stainless steel substrate is a mixture of $H_3PO_4$ and $H_2SO_4$. Preferred solution for Pt—Ir substrate is $CaCl_2$ or a mixture of NaOH and NaCN. To minimize capillary action between the etching solution and the wire, the etching solution is preferably equilibrated in gel (e.g., agar), and the surface of the gel is covered by an oil layer. The gel "captures" the salt solution in small pores and the dissolution of the salts in the oil layer are negligible. This treatment prevents flooding of solution caused by capillary action and thus enabling fixing a precise coordinate of the interface solution-metal.

The geometry of the tip (see, e.g., angles $\theta_1$ and $\theta_2$ in FIGS. 1*a-b*) can be shaped by controlling the rate of chemical etching profile, R(z, t) and the current density profile, I(z, t), through the dipped length of the substrate. The control on these profiles is achieved by the data processor (via the controller) which is supplemented by an algorithm for calculating the parameters for the process. These parameters include, without limitation, the frequency and amplitude of voltage/current waves, applied between the substrate and a reference electrode in the etching solution, the offset and shape of the waves, the dipped portion, x(t), of the substrate inside the etching solution, the velocity, v(t), of the substrate relative to the etching solution. Additionally, the geometry of the tip can be adjusted by altering the chemical composition, pH and viscosity of the etching solution.

In various exemplary embodiments of the invention the method continues to step 63 in which one or more intermediate layers are formed. The intermediate layer can comprise, as stated, a transition metal, a porous conductive polymer and the like. When the intermediate layer comprises is a porous conductive polymer, such as, but not limited to, nanotubes, the formation of the nanotube layer is preferably preceded and more preferably both preceded and followed by deposition of atomic layers of palladium so as to reduce or eliminate the aforementioned Schottky barrier. As stated, the intermediate layer can be formed between any two layers of the electrode device. In a more preferred process, step 63 comprises a first substep in which one or more atomic layers of palladium are deposited on the substrate, a second substep in which one or more layers of nanotubes are deposited on the deposited palladium layer(s), and a third substep in which one or more atomic palladium layers are deposited on the nanotubes layer(s).

When the nanotubes comprise SWNT, it can be deposited on the substrate, for example, by CVD process [Li et al., 1996, Science 274, 1701; J. C. P. Gabriel, 2003, Mater. Res. Soc. Symp. Proc. 762, Q.12.7.1, Bradley et al., 2003, Nano Lett. 3, 639].

When the nanotubes comprise metal nanotubes, they can be deposited on the substrate by electrochemical deposition techniques using filter template such as gold membrane nanotubes and polycarbonate membrane filter template (15-200 nm in pore diameter) [Fukunaka et al., 2006, Electrochem. Solid-State Lett 9(3):C62-C64; Wirtz et al., 2002, Chemistry—A European Journal 8(16):3572-3578; C. R. Martin and D. T. Mitchell, in *Electroanalytical Chemistry* Vol. 21, A. J. Bard and I. Rubinstein (Eds.), Marcel Dekker: NY, 1999; C. N. R. Raw and M. Nath, 2003, *Dalton Trans.*, 1-25; Sehayek et al., 2003, *J. Am. Chem. Soc.* 125:4718-4719].

The method continues to step 64 in which the substrate is at least partially coated by one or more metal alloys, so as to provide one or more metallic layer having a nanometric pattern thereon. The metal alloy preferably comprises at least two metals each can be a transition metal, a rare earth metal or an alkali metal. For example, the metal alloy can comprises a noble metal, such as, but not limited to, Pt, Pd, Rh, Re, Au and Ir. Alternatively or additionally, the metal alloy can comprise a metal which is capable of producing a stable oxide element, such as, but not limited to, $TiO_2$, $Ta_2O_5$, NiO, $Al_2O_3$, IrO, $IrO_2$ and $IrO_3$. Further, the metal alloy can comprise a reactive metal, including, without limitation, Mo and W. In various exemplary embodiments of the invention the substrate is coated by a metal alloy nitride compound, such as, but not limited to, $Pt_{y1}Pd_{y2}Rh_{y3}Re_{y4}Au_{y5}Ir_{y6}Ti_{y7}Ta_{y8}Ni_{y9}Al_{y10}W_{y11}Mo_{y12}N_{y13}$, where $y_1$, $y_2$, $y_3$, $y_4$, $y_5$, $y_6$, $y_7$, $y_8$, $y_9$, $y_{10}$, $y_{11}$, $y_{12}$ and $y_{13}$ are the contents of each element in the compound, and can represent any percentage from 0% to 100%.

The substrate can be coated by one or more metallic layers. In the case of multilayer, the first layer on the substrate serves for improving the adhesion and microstructure of the upper layers. The coating can be performed by physical vapor deposition (PVD), chemical vapor deposition (CVD), atomic layer deposition (ALD), electrochemical plating (ECP) and the like. In the case of more than one metallic layers, the first layer can be deposited formed by PVD, ALD or by electrochemical plating, such as, but not limited to, plating of gold on tungsten or plating of platinum on stainless steel. The second layer can be electro-plated on the first layer such as, but not limited to, plating of iridium on gold or platinum layer.

For example, in one embodiment, an intermediate gold layer is applied on a tungsten substrate and a superficial layer of $IrO_2$ or other metals alloys such as the aforementioned metal alloy nitride compound is applied on the gold layer. In another embodiment, an intermediate platinum layer is applied on a stainless steel substrate and a superficial layer of $IrO_2$ or other metals alloys such as the aforementioned metal alloy nitride compound is applied on the platinum layer.

Any of the above coating techniques are well known to those skilled in the art of coating and in particular thin film deposition. In CVD, for example, the metallic layers are formed by placing the substrate in a mixture of gases. Under certain pressure and temperature conditions, the molecules contained in the gases are deposited on the surfaces of the substrate as a result of thermal reactions to form a to form the metallic layer thereupon. CVD process can be done in a conventional CVD reactor such as, for example, the CVD reactor disclosed in U.S. Pat. Nos. 5,503,875, 5,441,570, and 6,983,620.

In ALD, the metallic layers are formed on the substrate by chemically sorbing one or more precursors which comprise the desired metal and a ligand onto the substrate surface to form a monolayer of precursors that is approximately one molecule thick. A second precursor may be introduced to chemically react with the first chemisorbed layer to grow a thin film on the substrate surface. After sufficient process cycles of monolayer formation has occurred, or alternatively with the formation of the monolayers, the monolayers can be contacted with a reaction gas to form the metallic layer on the surface of the substrate. ALD process can be done in any ALD reactor such as, for example, the CVD reactor disclosed in U.S. Pat. Nos. 6,787,463, 6,808,978, 6,869,876 and 7,037,574.

In an ECP, a seed layer is first formed over the surface of the substrate and subsequently the substrate is exposed to an electrolyte solution while an electrical bias is simultaneously applied between the substrate and an anode positioned within the electrolyte solution. The electrolyte solution is generally rich in ions to be plated onto the surface of the substrate.

Therefore, the application of the electrical bias causes the ions to be urged out of the electrolyte solution and to be plated onto the seed layer. ECP process can be done in any way known in the art such as, for example, the techniques disclosed in U.S. Pat. Nos. 6,492,269, 6,638,409, 6,855,037 and 6,939,206.

In PVD, the metallic layers are deposited on the substrate by physical, as opposed to chemical, means. Typically, the deposition of the metallic layer is by sputtering, in which ions are created by collisions between gas atoms and electrons in a glow discharge. The ions are accelerated and directed to a cathode of sputter target material by an electromagnetic field causing atoms of the sputter target material to be ejected from the cathode surface, thereby forming sputter material plasma. By contacting the substrate with the plasma, the metallic layers are deposited on the surface of the substrate. PVD process can be done in any conventional magnetron, such as the magnetron described by J. A. Thornton in various publications (to this end see, e.g., Thornton et al., "Thin Film Processes", edited by J. L. Vossen and W. Kern, pp 75-113, Academic Press, New York, 1978; Thornton et al., "Tubular Hollow Cathode Sputtering onto Substrates of Complex Shape", 1974, J Vac Sci Technol 12:93-97; and Thornton, "Hollow Cathode Magnetron Sputtering of Metallurgical Coatings", 1984, Zeitschrift fur Metallkunde 75:847-854).

Several processes and techniques of PVD and CVD, such as reactive sputtering process (RS) and arc cathode (ARC) techniques, are now widely used as wear-resistant coatings for cutting tools and metallic machine elements. Films produced by these techniques have low friction coefficients and low wear rates. At low temperature (lower than about 100° C.), the adhesion of the films to the substrate is very poor. Good adhesion is achieved only at higher temperature (higher than 350° C.). However, at these temperatures a substrate of micrometric size is irreversibly damaged due to its low mass. It is recognized that the RSP and ARC techniques cannot employed for micrometric size substrate (below about 125 μm), without damaging the substance and/or causing irreversible structure and morphological changes to the tip. Thus, heretofore RSP and ARC techniques were only used to produce films, such as TiN films, on thick substrates with sufficient mass so as to allow evacuation of heat.

While reducing the present invention to practice it was uncovered that these problems can be overcome using a magnetron system 100 which allows the cooling of the substrate during the deposition of the metallic layer thereupon.

Reference is now made to FIG. 6, which is a schematic illustration of magnetron coating system 100 for coating the substrate with one or more sputter materials, e.g., a metal alloy. System 100 can be used for executing step 64 of the method of the present embodiments.

In its simplest configuration, system 100 comprises a magnet 130, for generating a magnetic flux within a deposition chamber 134 having a wall 11, and a gas delivery unit, 116 for providing a flow of sputter gas into chamber 134. Preferably, but not obligatorily, chamber 134 has a round shape, e.g., a cylindrical shape. System 100 further comprises a plurality of local magnet assemblies 102 positioned outside chamber 134 and respectively defining a plurality of treating zones 136 within chamber 134. A serial arrangement of four treating zones is shown in FIG. 6, but it should be understood that any number of treating zones in any arrangement is contemplated. The magnet assemblies 102 are preferably pairs of coaxial cylindrical magnets which can be either balanced or unbalanced magnets.

Each treating zone comprises a cathode of sputter target material 106 and one or more anodes 104 in proximity to target material 106. In various exemplary embodiments of the invention there are two anodes which are positioned on both sides of the target material. Typical dimensions for the treating zones are about 15-25 cm in diameter and about 8-14 cm in height. Typical dimensions for chamber 134 are about 15-25 cm in diameter and about 40-250 cm in height. The typical diameter of the main magnet 130 is about 15-25 cm.

The treating zones and the magnet assemblies thus form a plurality of magnetron subunits 132, which can operate synchronically or independently as desired. The operation of the individual magnetron subunits, as well as magnet 130 and gas delivery unit 116 is optionally and preferably controlled by a control system 122, as further detailed hereinunder. Different subunits can contain different target materials. The target materials are typically shaped as cylinders with a typical inner diameter of about 15-25 cm and a typical height of about 4-10 cm. Different subunits can contain different target metals. The target material can be any metal or any metal alloy. Additionally, the target materials can be formed of several cylindrical segments, each of a different metal or metal alloy.

Magnet 130 is preferably configured to apply axial magnetic field, which is guided into chamber 134 by anodes 104. This magnetic field is combined by the superposition principle with the magnetic field generated by the local magnet assemblies 102. The flux area of the combined magnetic field (also referred to as "the racetrack") preferably covers approximately 50-90% of the area of each target material 106. The intensity of magnetic field for the main magnet and the local magnet assemblies is optionally and preferably controlled by a control system 122. In various exemplary embodiments of the invention system 122 provides independent control to each local magnet assembly 102.

Preferably, high intensity magnetrons are used as magnets 130 and 122, and the control over intensity of magnetic field is achieved by shielding the magnetic field to provide the desired intensity. The intensity the overall magnetic field in each magnetron subunit is typically from about 200 Gausses to about 800 Gausses.

An AC power source 124, which is optionally and preferably controlled by system 122, is configured to supply voltage to the cathodes of sputter target material, such as to form an electric field which is sufficiently high to ionize atoms of the gas provided by unit 116 and also the plasma of the target. A preferred gas is $N_2$, but other types of gasses, such as argon is a carrier gas, not deposit in the alloy film, are not excluded. Typically, power source 124 provides power of about 100-3000 Watts and frequency of about 25-300 KHz to the cathodes. For thin substrate, e.g., below 50 μm in diameter, the power is preferably less than 1000 Watts so as to prevent excess of substrate heating.

As a result of the electromagnetic draft force caused by the electric field and the magnetic field, the ions of the gas collide with the sputter target material and sputter material plasma is generated in the treating zones.

System 100 further comprises a movable plate 114 configured to hold the substrate (not shown). Plate 114 can move within chamber 134 in any direction. Specifically, plate 114 can move reciprocally along the longitudinal direction (generally shown in FIG. 6 as the z direction), e.g., a long a shaft 110 and/or the transverse direction (generally shown in FIG. 6 as the r direction), e.g., along a shaft 109. Thus, plate 114 can move within lateral planes (perpendicular to the z direction) as well as from one lateral plane to the other. For example, plate 114 can perform cycling movement through or between the treating zones. The motion of plate 114 can be established by means of a motor 118 which is optionally and preferably controlled by system 122.

With the motion of plate 114 the substrate moves one treating zone to the other, contacts the sputter material plasma present in the treating zones, and being gradually coated by the sputter material. The substrate is therefore subjected to a non-continues sputtering deposition process.

The velocity profile of the plate, $v(z, t)$, is selected according to the desired characteristic of the deposited layer. Specifically, lower velocities are applied when the required content and size are high, and higher velocities are applied when the required content and size are low.

In various exemplary embodiments of the invention, treating zones 136 are spaced apart to form a plurality of cooling zones 138 therebetween. The separation s between two successive treating zones (and therefore longitudinal dimension of individual cooling zones) is preferably selected such that the temperature, sputter material plasma concentration and/or electromagnetic draft force is sufficiently low. This ensures that when the substrate visits a cooling zone the extent of the sputtering deposition process is reduced. Within cooling zones 138 the motion of plate 114 can be reduced or even ceased for predetermined intervals, to allow sufficient cooling of the substrate. A typical separation s between two successive treating zones is from about 5 cm to about 30 cm.

The motion of plate 114 within chamber 134 is preferably performed in cycles. One complete cycle can be defined, for example, between two successive visits of plate 114 in a given treating zone while having the same longitudinal component of the velocity, or between two successive visits of plate 114 in the first or last treating zone of chamber 134. The reciprocal of the duration of each such cycle is referred to herein as the frequency of motion of plate 114. To obtain vast population of particles in a nanometric scale, the frequency of motion of plate 114 is preferably high compared to the deposition rate in the chamber. Typically, the duration of each cycle is of a few minutes. According to a preferred embodiment of the present invention the accumulated time in which the substrate occupies the cooling zones in each cycle is from about 10% to about 50% from the cycle's period.

To prevent excess of heat, for thin substrate the velocity near the cathode of the magnetron subunit is preferably high. Additional consideration can be made with respect to the motion of plate 114 in the lateral planes. In various exemplary embodiments of the invention the transverse coordinate of the substance within the treating zones is selected in so as to control the temperature of the substrate. Denoting the center of the subunit more precisely the center of the cylindrical target as $(r, z)=(0, 0)$, the temperature profile of the subunit increases with r and decreases with z. Thus, a thin substrate is preferably kept near r=0 to prevent excess heating of the substrate.

The vacuum level at the chambers is maintained by a vacuum controller 126, which is typically manufactured as a vacuum port and a pump. Preferably, the operation of vacuum controller 126 is also controlled by system 122.

In various exemplary embodiments of the invention magnetron system 100 comprises a fine particle separator 108, which can be, for example, a cylindrical metallic membrane. Separator 108 is preferably removable from the chamber, so as to allow its replacement. Thus, the porosity of separator 108 is selected according to the size of particles which is required in the respective subunit.

A cooling mechanism 120, which can be, for example, one or more cooling pipes, is positioned in thermal communication with the subunit for controlling the temperature and preventing overheating. Cooling mechanism 120 is optionally and preferably controlled by system 122. For example, when the cooling mechanism is an arrangement of cooling pipes, system 122 can control the flow rate of the cooling fluid in the pipes.

The internal wall of the chamber and the anode surfaces are preferably covered by a film of reactive metal. At the end of the deposition process, the films are preferably removed to a recovery system for extracting the noble metals therefrom. This can be done, for example, by electrochemical etching using a suitable etching solution, such as, but not limited to, $KOH$ and $NaNO_2$.

System 100 is suitable for coating many materials, both metallic and organic, at a wide range of diameters, from about 1 µm to about 500 µm. System 100 is also suitable for coating substances of various shapes, including, without limitation, tapered substrates and sharp tips. Substrates of the above materials, dimensions and shapes can be coated using system 100 with minimal or no damage or morphological change to the substrate. Unlike previous techniques of PVD where a significant amount of sputter materials are dissipated on the walls of the deposition chamber, the process of the present embodiments ensures higher efficiency of sputter due to the cylindrical configuration and due to the recovery of noble materials.

The metal elements have different physico-chemical properties such as crystal structure, density, electro-negativity, electrical conductance, heat capacitance and heat conductivity. In the PVD process, bond formation, crystal structure, particle size and rate of deposition of these particles of elements from the plasma to the substrate are specific and different from one metal to another. This leads to different sized population of deposit particles of elements and to the formation of the nanometric pattern on the metallic layer. Typically the population size of the particles is from sub nanometer to tens of nanometers.

According to a preferred embodiment of the present invention the coating process is performed such as to provide the metallic layer a predetermined roughness and porosity, hence to form the desired nanometric pattern thereon. The population of particles in each subunit of system 100 depends on several parameters, which include, without limitation, the velocity profile of plate 114, the intensity of applied magnetic fields, the AC power, the vacuum level in the chambers, the gas flow rate from unit 116, and the cooling rate of cooling mechanism 120. These parameters can be judiciously selected, monitored and controlled by system 122, independently for each subunit. Thus, the present embodiments successfully provide a technique for controlling the roughness and porosity of the metallic layers.

Referring now again to FIG. 4, the method preferably continues to step 65 in which an electrochemical etching procedure is applied to the metallic layer so as to increase its porosity. The roughness and porosity of the metallic layer can also be controlled by judicious selection of the content of the extracted particles of the reactive element in the deposit alloy. Thus, the electrochemical etching procedure extracts out the selected particles of the reactive metal elements from the nanometric pattern. In various exemplary embodiments of the invention the electrochemical etching is done using the setup illustrates in FIG. 5. Preferred etching solution is a mixture of $KOH$ and $NaNO_2$. The charge densities are preferably selected such that only the reactive elements are etched while other elements remain on the substrate.

When calculating the appropriate charge density, the interfacial area of the tip is to be considered (as oppose to the geometric area). Noble metals, such as Pt can tolerate a maximal charge density of about 500 µC/cm$^2$, $Ta_2O_5$ can tolerate a maximal charge density of about 1000 µC/cm$^2$, and Tungsten and Mo can tolerate a maximal charge density of about 50 $\mu C/cm^2$. Thus the preferred charge density that is needed to extract the reactive metals is from about 50 $\mu C/cm^2$ to about 100 $\mu C/cm^2$, depending on time of extraction.

The method, optionally and preferably continues to step 66 in which the metallic layer is activated so as to ensure that the surface of the metallic layer is electrochemically active. The purpose of this optional step is to obtain stable oxide components such as, but not limited to, $TiO_2$, $Ta_2O_5$, $NiO$, $Al_2O_3$, $IrO$, $IrO_2$ and $IrO_3$.

The activation step 66 can be done, for example, by immersing the coated substrate in saline phosphate buffer and applying a voltage gradient, namely a potential difference between the coated substrate and a reference electrode, e.g., such Ag/AgCl. The voltage gradient is preferably from a value above the reduction of water, (e.g., above −0.95 volts), to a value above the oxidation of water (e.g., above 0.65 volts (the limits for electrolysis of water is from about −0.95 to about 0.65 volts versus Ag/AgCl).

In various exemplary embodiments of the invention the method continues to step 67 in which the metallic layer is subjected to an aging process so as to remove unstable residues from the layer.

The aging process preferably comprises two process steps. In a first step the coated substrate is soaked in boiling deionized distilled water, typically for few hours. The distilled water can be supplemented by $H_3PO_4$ to increase the efficiency. In a second step of the aging process the coated substrate is subjected to prolonged pulsing in saline phosphate buffer. This step can be done using cathodic-first biphasic pulses.

Once the substrate is coated by implementation of one or more of the above steps, an electrically conductive core is provided.

The method then continues to step 68 in which the metallic layer is coated by one or more electrically isolating layers. The electrically isolating layer preferably comprises a biocompatible polymer such as, but not limited to, Parylene-C or Polyimide, or an inorganic insulator such as, but not limited to, glass or quartz. In both cases the coating can be performed by PVD. Because one molecule is deposited at a time, the coating forms slowly and uniformly over the surface of the conductive core substantially with no pinholes even in sub-micron thickness. Spontaneous polymerization eliminates potentially toxic impurities such as catalyst and plasticizers and inhomogeneities in film structure. It is to be understood that it is not intended to limit the scope of the present invention to PVD. Inorganic insulation, for example, can be done by pulling technique as known in the art.

The thickness of the electrically isolating layer can vary. For PVD coating the thickness is from about 10 nm to several microns, and for pulling technique the thickness is from several microns to hundreds of microns.

Step 68 is employed in a manner such that the metallic layer is at least partially exposed at its tip. This can be done in more than one way. In one embodiment, masking is employed. Specifically, the tip is coated by metallic layer(s) while the remainder of the substrate or conductive core is coated by the electrically isolating layer. An electrode device manufactured according to this embodiment is illustrated in FIG. 1*a* above.

In another embodiment, the process does not include masking. The entire conductive core is coated by one or more the electrically isolating layers. In this embodiment, the method preferably continues to optional step 69 in which the tip is exposed. Step 69 can be executed in any way known in the art, such as, but not limited to, using a laser beam or a heat beam of microforge. An electrode device manufactured according to this embodiment is illustrated in FIG. 1*b* above.

Selected steps of the above steps can be repeated one or more times to provide a plurality of electrode devices. These electrode devices can then be assembled to provide an electrode assembly. Thus, according to a preferred embodiment of the present invention the method continues to step 70 in which the plurality of electrode devices are assembled. The electrode devices can be assembled, for example, into clusters of 2-10 electrode devices, depending on the diameters of the electrode devices. Such clusters can be formed by wrapping the electrode devices around each other. Several clusters, e.g., 2-10 clusters can then be fixed together by holders connected to the edges of the clusters. Tension force can be applied between the holders for straightening the clusters. The configuration of clusters can then be subjected to the aforementioned process of coating by electrically isolating layers (see step 68) to form a bundle of electrode structures. Due to masking of the holders, the edges of the clusters are not coated. Additionally, several bundles can be assembled together by wrapping, holders or coating as described above.

The flexibility and stiffness of the electrode assembly can be controlled by the number of electrode devices in the cluster, the thickness of insulation of the cluster, the number of clusters, the thickness of insulation of the bundle, the number of bundles and the thickness of insulation of the electrode assembly. Higher level of flexibility can be achieved by masking several nodes through the length of the clusters, bundles and/or electrode assembly, such that the nodes are not further coated.

The method ends at step 71.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An electrode device, comprising an electrically conductive core of micrometric size further comprising: a) a substrate and b) a metallic layer having a porosity and a nanometric pattern thereon; said electrically conductive core coated by at least one electrically isolating layer; said metallic layer being at least partially exposed at a tip of said electrically conductive core wherein, the thickness of said at least one metallic layer is configured as desired, the porosity and the nanometric pattern spread substantially in the whole volume of said at least one metallic layer of said exposed tip, including homogenous spreading or any profile of spreading of said porosity and nanometric pattern, said porisivity is up to 90%.

2. An electrode assembly, comprising at least one bundle of electrode devices, at least one electrode device being the electrode device of claim 1, wherein, said at least one metallic layer of said at least one electrode device comprising of a nanometric mosaic of at least of two kinds of metals or metal alloy nanoparticles, said mosaic is configured in any plane or orientation, said at least one kind of metal or metal alloy nanoparticle of said at least one metallic layer being selectively extracted in nanometric scale without affecting said micrometric size of said exposed tip of said at least one electrode device, while at least one kind of metal or metal alloy nanoparticle of said at least one metallic layer being maintained as a metallic network backbone of spongy durable structure, said at least one electrode device is capable of maintaining a charge density as desired more than 600 $mC/cm^2$ in long-term of continuous stimulation.

3. An implantable stimulation device for delivery of electrical stimuli to a neurological location, the implantable stimulation device comprising: at least one bundle of flexible electrode devices disposed in a guiding encapsulation, at least one electrode device being the electrode device of claim 2; and a plurality of microwires, connected to said at least one bundle of flexible electrode devices such that electrical communication is established in an addressable manner between each microwire and at least one electrode device.

4. An implantable device for communicating with said implantable stimulation device according to claim 3, the implantable device comprising an implantable device body having therein a multi-channel system capable of providing stimulation signals and receiving sensing signals via a plurality of microwires, and a memory medium communicating with said multi-channel system and configured to store, at least temporarily, a stimulation protocol and/or said sensing signals; wherein said multi-channel system is designed and configured to provide said stimulation signals based on said sensing signals and using said stimulation protocol.

5. The device of claim 3, wherein said at least one bundle of flexible electrode devices are disposed in said guiding encapsulation in a manner such that when a pressure is applied on said plurality of microwires, said flexible electrode devices fan outward from said guiding encapsulation to define a target region which is substantially larger than a cross-sectional area of said guiding encapsulation, said fanning out of said electrode devices is accomplished due to elastic forces present between adjacent electrode devices.

6. The device of claim 3, wherein said guiding encapsulation is removable and comprising of: (a) a plurality of disconnectable parts; and (b) means of disconnecting said parts.

7. The device of claim 3, wherein said guiding encapsulation comprising of biodegradable material.

8. The electrode device according to claim 7, wherein said at least one metallic layer is capable of preventing penetration of macromolecules therethrough, said at least one metallic layer having a nanostructure excluding macromolecules, and allowing penetration of small electrolytes with partition coefficient close to unity.

9. A system for delivery of electrical stimuli to a neurological location, comprising: (a) a first implantable device, comprising at least one bundle of flexible electrode devices disposed in a guiding encapsulation, at least one electrode device being the electrode device of claim 2, and a plurality of microwires connected to said at least one bundle of flexible electrode devices such that electrical communication is established in an addressable manner between each microwire and at least one electrode device; and (b) a second implantable device comprising an implantable device body having therein a multi-channel system capable of providing stimulation signals to said first implantable device and receiving sensing signals from said first implantable device, and a memory medium communicating with said multi-channel system and configured to store, at least temporarily, a stimulation protocol and/or said sensing signals, wherein said multi-channel system is designed and configured to provide said stimulation signals substantially in real time based on said sensing signals and using said stimulation protocol.

10. The system of claim 9, further comprising a wireless communication system for establishing communication between said memory medium and an external nonimplantable data processor.

11. The system of claim 10, further comprising said external nonimplantable data processor.

12. The system of claim 11, wherein said data processor is supplemented by an algorithm capable of calculating said stimulation protocol based on said sensing signals, said stimulation protocol being transmitted by said data processor via said wireless communication system to be stored in said memory medium.

13. The system of claim 12, further comprising a mechanism for controlling pressure applied on said plurality of microwires to extrude at least a portion of said flexible electrode devices outward from said guiding encapsulation.

14. The device of claim 2, wherein said nanometric pattern is selected so as to ensure that the surface area of said electrically conductive core is larger than the geometric surface area of said electrically conductive core by at least one order of magnitude.

15. The device of claim 2, wherein said nanometric pattern is selected so as to ensure that the surface area of said electrically conductive core is larger than the surface area of said substrate by at least one order of magnitude.

16. The device of claim 2, wherein said electrode device is capable of sensing electrical signals at a signal-to-noise ratio of at least 300.

17. The device of claim 2, wherein the porosivity of said at least one metallic layer is up to 90%, and pore size of said metallic layer is up to more than 200 nm.

18. The device of claim 1, wherein said electrically conductive core further comprises at least one intermediate layer.

19. The device of claim 1, wherein said at least one metallic layer comprises at least one intermediate metallic layer and at least one superficial metallic layer.

20. The device of claim 1, wherein said electrode device is capable of maintaining a charge density as desired more than 600 $mC/cm^2$.

21. The electrode device according to claim 1, wherein said at least one metallic layer comprising of nano tubes having a low Schottky energy barrier.

* * * * *